US009435795B2

(12) United States Patent
May et al.

(10) Patent No.: US 9,435,795 B2
(45) Date of Patent: *Sep. 6, 2016

(54) ENHANCED DEPOSITION OF CHROMOGENS UTILIZING PYRIMIDINE ANALOGS

(71) Applicant: Ventana Medical Systems, Inc., Tucson, AZ (US)

(72) Inventors: Eric J. May, Chandler, AZ (US); Adrian E. Murillo, Tucson, AZ (US); Jerome W. Kosmeder, II, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/507,447

(22) Filed: Oct. 6, 2014

(65) Prior Publication Data

US 2015/0024405 A1  Jan. 22, 2015

Related U.S. Application Data

(63) Continuation of application No. 13/339,066, filed on Dec. 28, 2011, now Pat. No. 8,871,442.

(60) Provisional application No. 61/460,349, filed on Dec. 30, 2010.

(51) Int. Cl.
   *G01N 33/53* (2006.01)
   *C12Q 1/68* (2006.01)
   *G01N 33/58* (2006.01)

(52) U.S. Cl.
   CPC ........ *G01N 33/5306* (2013.01); *G01N 33/581* (2013.01)

(58) Field of Classification Search
   CPC .................. G01N 33/5306; G01N 33/581
   USPC .............................. 435/6.1, 7.1, 7.2; 422/430
   See application file for complete search history.

(56) References Cited

U.S. PATENT DOCUMENTS

| 4,275,149 A | 6/1981 | Litman et al. |
| 4,318,980 A | 3/1982 | Boguslaski et al. |

(Continued)

FOREIGN PATENT DOCUMENTS

| EP | 0 977 033 | 2/2000 |
| JP | A 64-021341 | 1/1989 |

(Continued)

OTHER PUBLICATIONS

Naguib et al., "Structure-Activity Relationships for the Binding of Ligands to Xanthine or Guanine Phosphoribosyl-Transferase from *Toxoplasma gondii*," *Biochemical Pharmacology* 50(10):1685-1693, 1995.

(Continued)

*Primary Examiner* — Jezia Riley
(74) *Attorney, Agent, or Firm* — Ventana Medical Systems, Inc.

(57) ABSTRACT

This disclosure relates to compositions that enhance the deposition of detectable moieties on tissue samples, methods utilizing these compositions and kits including these compositions. The compositions include a deposition enhancer having a formula

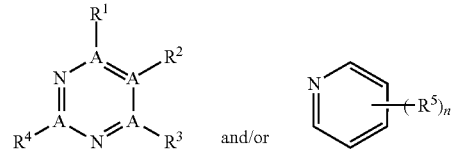

and/or where $R^1$, $R^2$, $R^3$, and $R^4$ are independently selected from aliphatic, aryl, halogen, a heteroatom-containing moiety, and hydrogen; $R^1$ and/or $R^3$ can be bound to $R^2$ to form a fused, aromatic ring system; $R^5$ is selected from a heteroatom-containing moiety; A is selected from, a carbon atom, a heteroatom, other than sulfur, and any combination thereof; n is 1-5, an enzyme, a specific binding moiety and a detectable moiety.

39 Claims, 21 Drawing Sheets

(56) References Cited

U.S. PATENT DOCUMENTS

| | | | |
|---|---|---|---|
| 5,043,266 | A | 8/1991 | Dewars et al. |
| 5,225,325 | A | 7/1993 | Miller et al. |
| 5,650,327 | A | 7/1997 | Copeland et al. |
| 5,654,200 | A | 8/1997 | Copeland et al. |
| 5,795,808 | A | 8/1998 | Park |
| 5,800,988 | A | 9/1998 | Casterman et al. |
| 5,840,526 | A | 11/1998 | Casterman et al. |
| 6,005,079 | A | 12/1999 | Casterman et al. |
| 6,015,695 | A | 1/2000 | Casterman et al. |
| 6,036,969 | A | 3/2000 | Golz-Berner et al. |
| 6,296,809 | B1 | 10/2001 | Richards et al. |
| 6,352,861 | B1 | 3/2002 | Copeland et al. |
| 6,649,138 | B2 | 11/2003 | Adams et al. |
| 6,670,113 | B2 | 12/2003 | Hainfeld |
| 6,682,596 | B2 | 1/2004 | Zehnder et al. |
| 6,815,064 | B2 | 11/2004 | Treadway et al. |
| 6,827,901 | B2 | 12/2004 | Copeland et al. |
| 6,943,029 | B2 | 9/2005 | Copeland et al. |
| 7,642,064 | B2 | 1/2010 | Bieniarz et al. |
| 8,871,442 | B2 * | 10/2014 | May .................. G01N 33/5306 422/430 |
| 2003/0211630 | A1 | 11/2003 | Richards et al. |
| 2004/0052685 | A1 | 3/2004 | Richards et al. |
| 2004/0265922 | A1 | 12/2004 | Bieniarz et al. |
| 2005/0003462 | A1 | 1/2005 | Kaplan |

FOREIGN PATENT DOCUMENTS

| | | |
|---|---|---|
| JP | A H7-308200 | 11/1995 |
| JP | A 2000-46827 | 2/2000 |
| WO | WO 90/03370 | 4/1990 |
| WO | WO 91/13336 | 9/1991 |
| WO | WO 98/17781 | 4/1998 |
| WO | WO 00/55358 | 9/2000 |
| WO | WO 03/002733 | 1/2003 |
| WO | WO 2005/003777 | 1/2005 |

OTHER PUBLICATIONS

Young et al., "Purine Derivatives as Competitive Inhibitors of Human Erythrocyte Membrane Phosphatidylinositol 4-Kinase," *Journal of Medicinal Chemistry* 33(8):2073-2082, 1990.

European Examination Report from EPC Patent Application No. 11 813 853.6, dated Apr. 24, 2014.

Notice of Reasons for Rejection dated Jul. 15, 2014, from related Japanese Patent Application No. 2013-547631 (with English-language translation), 4 pages.

Written Opinion from International Application No. PCT/US2011/067481.

European Communication Pursuant to Article 94(3) EPC dated Jan. 5, 2015, from European Application No. 11813853.6 (4 pages).

Patent Examination Report No. 2 dated Apr. 27, 2015, from the Intellectual Property Office of Australia for Australian Patent Application No. 2011352251.

* cited by examiner

FIG. 23 FIG. 24
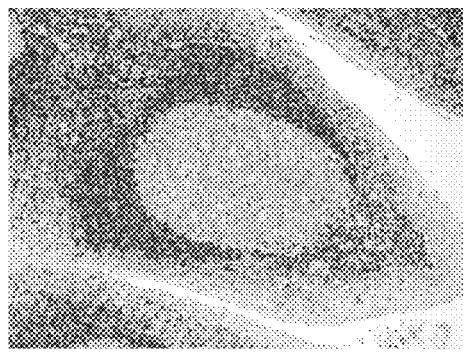
FIG. 25 FIG. 26
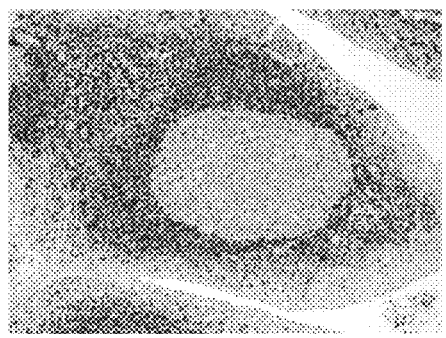
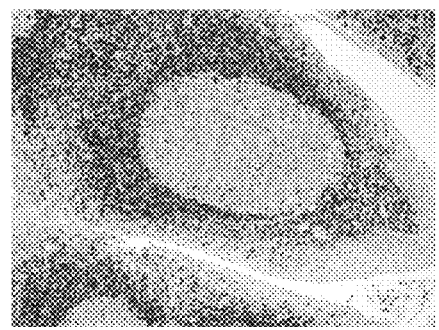

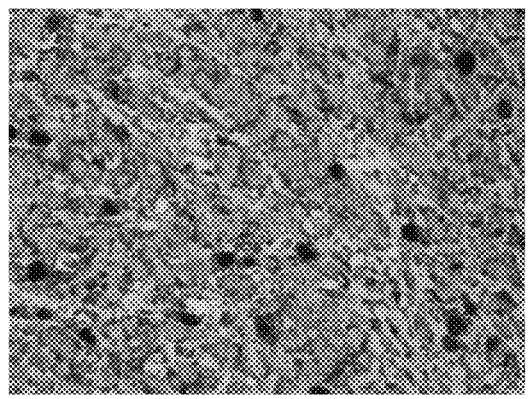 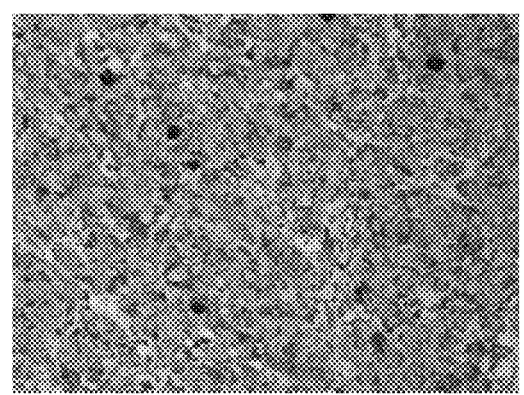
FIG. 29  FIG. 30

ENHANCED DEPOSITION OF CHROMOGENS UTILIZING PYRIMIDINE ANALOGS

CROSS-REFERENCE TO RELATED APPLICATION

This application is a continuation of U.S. patent application Ser. No. 13/339,066, which was filed on Dec. 28, 2011, which claims the benefit of the earlier filing date of U.S. Provisional Application No. 61/460,349, which was filed on Dec. 30, 2010. The entire disclosures of these prior applications are considered to be part of the disclosure of the present application and are hereby incorporated by reference.

FIELD

This disclosure relates to novel compositions containing pyrimidine analogs for use in increasing the deposition of detectable moieties on target molecules in a tissue.

BACKGROUND

Cell staining methods, including immunohistochemistry (IHC) and in situ hybridization analysis (ISH), are useful tools in histological diagnosis and the study of tissue morphology. IHC employs specific binding agents or moieties, such as antibodies, to detect an antigen of interest that may be present in a tissue sample. IHC is widely used in clinical and diagnostic applications, such as to diagnose particular disease states or conditions. For example, particular cancer types can be diagnosed based on the presence of a particular marker molecule in a sample obtained from a subject. IHC is also widely used in basic research to understand biomarker distribution and localization in different tissues. Biological samples also can be examined using in situ hybridization techniques, such as silver in situ hybridization (SISH), chromogenic in situ hybridization (CISH) and fluorescence in situ hybridization (FISH), collectively referred to as ISH. ISH is distinct from IHC, in that ISH detects nucleic acids in tissue whereas IHC detects proteins.

For in situ assays such as IHC assays and ISH assays of tissue and cytological samples, especially multiplexed assays of such samples, it is highly desirable to identify and develop methods which provide desirable results without background interference. One such method involves the use of Tyramide Signal Amplification (TSA), which is based on the patented catalyzed reporter deposition (CARD). U.S. Pat. No. 6,593,100, entitled "Enhanced catalyzed reporter deposition" discloses enhancing the catalysis of an enzyme in a CARD or TSA method by reacting a labeled phenol conjugate with an enzyme, wherein the reaction is carried out in the presence of an enhancing reagent.

While methods, such as those described above, have been employed to increase the signals obtained from assays, the results from these methods indicate that signal amplification is impaired by corresponding background signal amplification. Thus, the continued need exists for signal amplification that can produce optimal results without a corresponding increase in background signals.

SUMMARY

The present disclosure concerns a method for detecting a target in a sample by proximally depositing a marker, comprising: contacting the sample with a recognition solution, the recognition solution including a specific binding moiety specific to the target; labeling the specific binding moiety with an enzyme; contacting the sample with a detection solution, the detection solution comprising an enzymatic substrate so that the marker deposits proximally to the target in the presence of a deposition enhancer having a formula

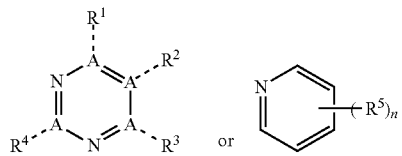

wherein $R^1$, $R^2$, $R^3$, and $R^4$ are independently selected from aliphatic, aryl, halogen, a heteroatom-containing moiety, and hydrogen; $R^1$ and/or $R^3$ can be bound to $R^2$ to form a fused, aromatic ring system; $R^5$ is a heteroatom-containing moiety; A is selected from a carbon atom, a heteroatom other than sulfur, and any combination thereof; n is 1-5; and detecting the marker. With reference to this method, contacting the sample with a detection solution may include enzymatically oxidizing the enzyme substrate using an oxidizing agent to form the marker. In particular disclosed embodiments, enzymatically oxidizing the enzyme substrate using an oxidizing agent comprises reducing the solubility or stability of the enzymatic substrate so that the enzymatic substrate becomes deposited as the marker.

In particular disclosed embodiments, the enzymatic substrate is selected from the group consisting of a chromogen and a tyramide-conjugate and the deposition enhancer may have a formula,

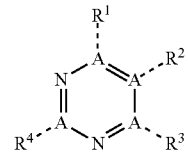

wherein $R^1$, $R^2$, $R^3$, and $R^4$ are selected from hydrogen and hydroxyl and each A is a carbon atom. In certain disclosed embodiments, $R^1$, $R^3$, and $R^4$ are hydrogen and $R^2$ is hydroxyl.

Other examples of the deposition enhancer include those having a formula,

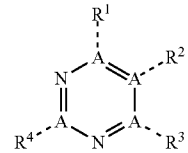

wherein $R^1$, $R^2$, and $R^3$ are independently selected from alkyl, alkene, alkyne, hydrogen, iodine, bromine, chlorine, fluorine, and combinations thereof.

Particular disclosed embodiments concern using an enzyme, which may be an oxidoreductase or a peroxidase. Additionally, the enzyme may be selected from horseradish peroxidase, glutathione peroxidase, and microoxidase. The disclosed specific binding moiety typically comprises an antibody or a nucleic acid.

With reference to the disclosed method, depositing the marker proximally to the target in the presence of the deposition enhancer includes the deposition enhancer at a concentration ranging from about 5 mM to about 15 mM.

In particular disclosed embodiments, the enzyme substrate may be selected from 1,3-diaminobenzidine, 3-amino-9-ethylcarbazole, tetramethylbenzidine, a fluorescein, a luminophore, a coumarin, a BODIPY dye, a resorufin, a rhodamine, or a derivative thereof. More typically, the enzyme substrate is a tyramine derivative.

When the sample is contacted with a detection solution, it is typically exposed to the enzymatic substrate at a concentration ranging from greater than 0 mM to about 8 mM. Also, the detection solution may further comprise an accelerator selected from a heteroaryl compound, a boronic acid, a phenolic compound, or a combination thereof. The heteroaryl compound may be selected from imidazole, L-histidine, pyridine N-oxide, pyrimidine N-oxide, N-methyl morpholine oxide, and 2,2,6,6-tetramethylpiperidine-1-oxyl. Also, the detection solution may further comprise a non-ionic surfactant selected from a polyoxyethylene lauryl ether having a formula $(C_2H_4O)_{23}C_{12}H_{25}OH$; polyoxyethylene (20) sorbitan monoalkylate, the monoalkylate comprising between 8 and 14 carbons; a linear secondary alcohol polyoxyethylene having a formula $C_{12-14}H_{25-29}O(CH_2CH_2O)_x$, wherein x equals an integer between 2 and 12; and polyoxyethylene octyl phenyl ether. In particular disclosed embodiments, the detection solution may further comprise an antioxidant selected from sodium bisulfate, sodium stannate, sodium metabisulfate, and combinations thereof, and/or a Group I or Group II metal-containing salt having a formula $MX_2$ or MX where M is a Group I or Group II metal selected from lithium, sodium, potassium, cesium, calcium, magnesium, strontium, and barium; and X is selected from fluoride, chloride, bromide, iodide, carbonate, hydroxide, and phosphate.

Also contemplated in the present disclosure is a composition for detecting a target in a sample by proximally depositing a marker, comprising a deposition enhancer having a formula,

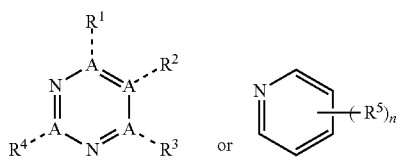

wherein $R^1$, $R^2$, $R^3$, and $R^4$ are independently selected from aliphatic, aryl, halogen, a heteroatom-containing moiety, and hydrogen; $R^1$ and/or $R^3$ can be bound to $R^2$ to form a fused, aromatic ring system; $R^5$ is a heteroatom-containing moiety; A is selected from a carbon atom, a heteroatom other than sulfur, and any combination thereof; n is 1-5; and an enzyme substrate.

In certain disclosed embodiments, the deposition enhancer has a formula,

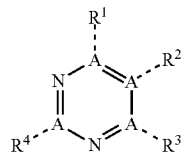

wherein $R^1$, $R^2$, $R^3$, and $R^4$ are selected from aliphatic, aryl, halogen, a heteroatom-containing moiety, and hydrogen; $R^1$ and/or $R^3$ can be bound to $R^2$ to form a fused, aromatic ring system; A is selected from a heteroatom, other than sulfur, a carbon atom, and combinations thereof. Typically, the deposition enhancer may have a concentration ranging from about 5 mM to about 15 mM and the enzymatic substrate has a concentration ranging from greater than 0 mM to about 8 mM, with the enzyme substrate being selected from 1,3-diaminobenzidine, 3-amino-9-ethylcarbazole, tetramethylbenzidine, a fluorescein, a luminophore, a coumarin, a BODIPY dye, a resorufin, a rhodamine, a tyramide, or a derivative thereof.

In particular disclosed embodiments, the composition may further comprise an accelerator selected from a heteroaryl compound, a boronic acid, a phenolic compound, or a combination thereof; a non-ionic surfactant selected from Brij® 35, TWEEN®, Tergitol™, and Triton™; and an antioxidant selected from sodium bisulfate, sodium stannate, sodium metabisulfate, and combinations thereof.

Also disclosed is a kit, comprising a detection solution, which comprises a deposition enhancer and an enzyme substrate, the deposition enhancer having a formula,

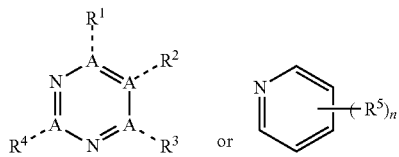

wherein $R^1$, $R^2$, $R^3$, and $R^4$ are independently selected from aliphatic, aryl, halogen, a heteroatom-containing moiety, and hydrogen; $R^1$ and/or $R^3$ can be bound to $R^2$ to form a fused, aromatic ring system; $R^5$ is a heteroatom-containing moiety; A is selected from a carbon atom, a heteroatom other than sulfur, and any combination thereof; n is 1-5.

In particular embodiments, the heteroaryl compound has a formula according to

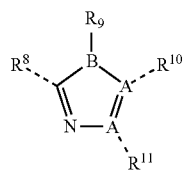

and/or a formula according to

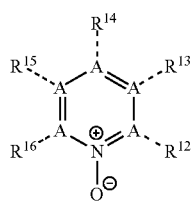

and/or a formula according to

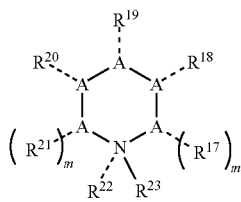

where $R^8$-$R^{22}$ independently are aliphatic, aryl, halogen, a heteroatom-containing moiety, hydrogen, or any combination thereof; $R^{23}$ is [O]. or [O]$^-$; A is a carbon atom, a heteroatom, other than sulfur, or any combination thereof; B is oxygen, carbon, or nitrogen; and m is 0-2. The halogen can be selected from iodine, bromine, chlorine or fluorine, and the heteroatom-containing moiety can be selected from hydroxyl, ether, silyl ether, ester, carboxylic acid, silyl, phosphonate, phosphine, amide, $NR^6R^7$ where $R^6$ and $R^7$ independently are hydrogen, aliphatic, aryl, heteroaliphatic, heteroaryl, or any combination thereof. In particular embodiments, $R^{17}$ and $R^{21}$ each comprise methyl group and m is 2. Exemplary heteroaryl compounds include, but are not limited to imidazole, L-histidine, pyridine N-oxide, pyrimidine N-oxide, N-methyl morpholine oxide, and 2,2,6,6-tetramethylpiperidine-1-oxyl.

In particular embodiments, the optional enhancer is a boron-containing compound, such as an organic boronic acid. Exemplary organic boronic acids include, but are not limited to boric acid.

In particular embodiments, the optional enhancer is a phenolic compound having a formula

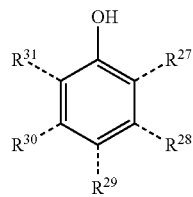

wherein $R^{27}$, $R^{28}$, $R^{29}$, $R^{30}$, and $R^{31}$ independently are can be selected from hydrogen, aliphatic, aryl, a heteroatom-containing moiety, or any combination thereof. The heteroatom-containing moiety is hydroxyl, ether, silyl ether, ester, carboxylic acid, silyl, phosphonate, phosphine, amide, and $NR^5R^6$ where $R^5$ and $R^6$ independently are hydrogen, aliphatic, aryl, heteroaliphatic, heteroaryl, and any combination thereof. In particular embodiments, any two adjacent groups selected from $R^{27}$, $R^{28}$, $R^{29}$, $R^{30}$, and $R^{31}$ can be bound to form a fused, aromatic or non-aromatic ring system. Exemplary phenolic compounds include, but are not limited to pyrocatechol.

In particular embodiments, the current method can further comprise: immobilizing the specific binding moiety-enzyme conjugate on the target in the sample; contacting the sample with a solution comprising a tyramide-hapten conjugate; contacting the sample with the enhancing solution; contacting the sample with the oxidant; and locating the target in the sample by detecting the tyramide-hapten conjugate. In particular embodiments, detecting the tyramide-hapten conjugate further comprises: contacting the sample with an anti-hapten antibody capable of recognizing and binding to the tyramide-hapten conjugate and a detectable moiety capable of being detected using deposition or fluorescent techniques; and detecting the detectable moiety. In particular embodiments, the tyramide-hapten conjugate comprises a hapten conjugated directly to tyramine or via a linker. Typically, the linker is aliphatic or heteroaliphatic.

The foregoing and features, and advantages of this disclosure will become more apparent from the following detailed description, which proceeds with reference to the accompanying figures.

BRIEF DESCRIPTION OF THE DRAWINGS

FIG. 14: no enhancement; FIG. 15: 100 mM imidazole, 50 mM boric acid; FIG. 16: 50 mM L-histidine, 10 mM pyrimidine; FIG. 17: 10 mM L-histidine, 10 mM 2-hydroxypyridine, 10 mM calcium chloride, 10 mM boric acid. Pathological scoring for signal/background was: FIG. 14, 3.75/0.5; FIG. 15, 4.0/0.75; FIG. 16, 4+/0.5; FIG. 17, 4/0.5.

FIGS. 23-26 are digital images of the IHC staining of bcl2 on tonsil tissue using the tyramide amplification system with and without enhancement of HRP oxidation for both tyramide and DAB deposition. FIG. 23: no enhancement for tyramide or DAB deposition; FIG. 24: no enhancement tyramide deposition, enhanced DAB deposition; FIG. 25: enhancement tyramide deposition, no enhanced DAB deposition; FIG. 26: enhancement tyramide and DAB deposition.

FIG. 29 is a digital image of ISH staining of the 18s ribosome on CaLu-3 xenograft tissues with 18s riboprobe, and an enhanced DAB with both 10 mM 2-hydroxypyridine and 10 mM L-histidine.

FIG. 30 is a digital image of ISH staining of 18s ribosome on CaLu-3 xenograft tissues with 18s riboprobe and no enhancement.

FIG. 43: no enhancement for tyramide or DAB deposition; FIG. 44: no enhancement tyramide deposition, enhanced DAB deposition; FIG. 45: enhancement tyramide deposition, no enhanced DAB deposition; FIG. 46: enhancement tyramide and DAB deposition.

DETAILED DESCRIPTION

I. Introduction

Figure 1:
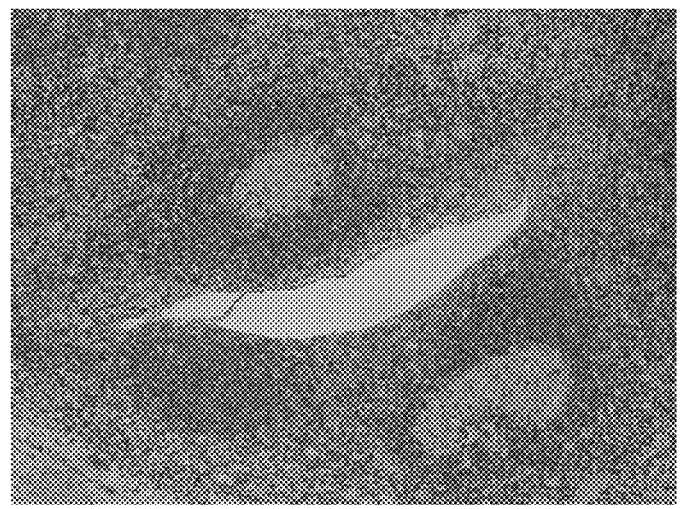
FIG. 1 is a digital image showing the IHC staining of bcl2 on tonsil tissue using a standard ultraView™ Detection Kit.

Diseases, such as cancer, can be diagnosed by a number of different methods. One method is to identify the presence of a biomarker, such as a cancer biomarker, in tissue or cells, the biomarker being correlated, or thought to be correlated, with a particular cancer type. Immunohistochemistry is oftentimes used to target protein biomarkers that are associated with a particular type of cancer, whereas in situ hybridization techniques are oftentimes employed to target nucleic acid sequences that are associated with a particular type of cancer.

Immunohistochemistry and in situ hybridization methods for target identification are becoming increasingly more important in research applications and for clinicians, for example for diagnostic and/or prognostic purposes. However, these techniques can be limited by the detectable signal emitted by a detection moiety that interacts or is deposited on the target molecule present or thought to be present in a tissue sample, such as a protein and/or a nucleic acid target molecule. Theoretically, one way to increase the signal obtained is to increase the deposition of a detectable moiety on target molecule, for example by increasing the rate of deposition, such that greater signal could be obtained in a shorter amount of time.

As disclosed herein, a novel formulation of a DAB chromogen acts synergistically to provide maximized DAB deposition during IHC or ISH tissue staining. The novel formulation of the DAB chromogen utilizes an organic enhancer as a buffer salt in combination with a variety of organic/inorganic enhancers and surfactant to synergistically maximize the DAB deposition and therefore signal. Also disclosed herein are methods of using the disclosed formulations to enhance IHC and/or ISH tissue staining.

The methods as described herein find utility for diagnostics, where results provided by the disclosed methods are used not only for diagnosis, but also for determining the optimal treatment, and tracking the progression and success of such treatment, in a clinical setting.

II. Terms

Unless otherwise noted, technical terms are used according to conventional usage. Definitions of common terms in molecular biology may be found in Benjamin Lewin, Genes VII, published by Oxford University Press, 2000; Kendrew et al. (eds.), The Encyclopedia of Molecular Biology, published by Blackwell Publishers, 1994); Robert A. Meyers (ed.), Molecular Biology and Biotechnology: a Comprehensive Desk Reference, published by Wiley, John & Sons, Inc., 1995; and George P. Rédei, Encyclopedic Dictionary of Genetics, Genomics, and Proteomics, 2nd Edition, 2003.

The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. A wavy line ("⌇"), is used to indicate a bond disconnection, and a dashed line ("- - -") is used to illustrate that a bond may be formed at a particular position.

Although methods and materials similar or equivalent to those described herein can be used to practice or test the disclosed technology, suitable methods and materials are described below. The materials, methods, and examples are illustrative only and not intended to be limiting.

The following explanations of terms and methods are provided to better describe the present disclosure and to guide those of ordinary skill in the art to practice the present disclosure.

Aliphatic: Moieties including alkyl, alkenyl, alkynyl, halogenated alkyl and cycloalkyl groups. A "lower aliphatic" group is a branched or unbranched aliphatic group having from 1 to 10 carbon atoms. This term encompasses substituted aliphatic compounds, saturated aliphatic compounds, and unsaturated aliphatic compounds.

Alkyl: A branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. The terms "halogenated alkyl" or "haloalkyl group" refer to an alkyl group as defined above with one or more hydrogen atoms present on these groups substituted with a halogen (F, Cl, Br, I). The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, etc.

The term "heterocycloalkyl group" is a cycloalkyl group where at least one of the carbon atoms of the ring is substituted with a heteroatom such as, but not limited to, nitrogen, oxygen, sulfur, or phosphorous. Optionally substituted groups, such as "substituted alkyl," describes groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxy, thiol and thioalkoxy.

Amplification: Amplification refers to the act or result of making a signal stronger. Amplification can be an increase in the magnitude of signal and/or in increase in the signal relative to the background, e.g. increased signal to noise ratio.

Antibody: Collectively refers to immunoglobulins or immunoglobulin-like molecules (including by way of example and without limitation, IgA, IgD, IgE, IgG and IgM, combinations thereof, and similar molecules produced during an immune response in any vertebrate, for example, in mammals such as humans, goats, rabbits and mice) and antibody fragments that specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4$ $M^{-1}$ greater or at least $10^5$ $M^{-1}$ greater than a binding constant for other molecules in a biological sample).

More particularly, "antibody" refers to a polypeptide ligand comprising at least a light chain or heavy chain immunoglobulin variable region which specifically recognizes and binds an epitope of an antigen. Antibodies can be composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of them well known in the art. Antibody fragments include proteolytic antibody fragments [such as F(ab')$_2$ fragments, Fab' fragments, Fab'-SH fragments and Fab fragments as are known in the art], recombinant antibody fragments (such as sFv fragments, dsFv fragments, bispecific sFv fragments, bispecific dsFv fragments, F(ab)'2 fragments, single chain Fv proteins ("scFv"), disulfide stabilized Fv proteins ("dsFv"), diabodies, and triabodies (as are known in the art), and camelid antibodies (see, for example, U.S. Pat. Nos. 6,015,695; 6,005,079; 5,874,541; 5,840,526; 5,800,988; and 5,759,808). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., Immunology, 3$^{rd}$ Ed., W.H. Freeman & Co., New York, 1997.

Typically, a naturally occurring immunoglobulin has heavy chains and light chains interconnected by disulfide bonds. There are two types of light chain, lambda and kappa. There are five main heavy chain classes (or isotypes) which determine the functional activity of an antibody molecule: IgM, IgD, IgG, IgA and IgE.

Each heavy and light chain contains a constant region and a variable region; the regions are also known as "domains." In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

Antigen: A molecule that stimulates an immune response. Antigens are usually proteins or polysaccharides. An epitope is an antigenic determinant composed of chemical groups or peptide sequences on a molecule that elicit a specific immune response. An antibody binds a particular antigen or epitope. The binding of an antibody to a particular antigen or epitope of an antigen can be used to localize the position of the antigen for example in or on a biological sample, or determine if the particular antigen is present in a biological sample. An antigen of interest is an antigen an IHC assay is designed to detect in a test sample. For example, to detect an antigen of interest, the primary antibody used in the IHC assay specifically binds to the antigen of interest.

An epitope is a site on a target molecule (e.g., an antigen, such as a protein or nucleic acid molecule) to which an antigen binding molecule (e.g., an antibody, antibody fragment, scaffold protein containing antibody binding regions, or aptamer) binds. Epitopes can be formed both from contiguous or juxtaposed noncontiguous residues (e.g., amino acids or nucleotides) of the target molecule (e.g., a protein-protein interface). Epitopes formed from contiguous residues (e.g., amino acids or nucleotides) typically are retained on exposure to denaturing solvents whereas epitopes formed by tertiary folding typically are lost on treatment with denaturing solvents. An epitope typically includes at least 3, and more usually, at least 5 or 8 10 residues (e.g., amino acids or nucleotides). Typically, an epitope also is less than 20 residues (e.g., amino acids or nucleotides) in length, such as less than 15 residues or less than 12 residues.

Aromatic: A term describing conjugated rings having unsaturated bonds, lone pairs, or empty orbitals, which exhibit a stabilization stronger than would be expected by the stabilization of conjugation alone. It can also be considered a manifestation of cyclic delocalization and of resonance.

Aryl: A substantially hydrocarbon-based aromatic compound, or a radical thereof (e.g. $C_6H_5$) as a substituent bonded to another group, particularly other organic groups, having a ring structure as exemplified by benzene, naphthalene, phenanthrene, anthracene, etc. This term also encompasses substituted aryl compounds.

Aryl alkyl: A compound, or a radical thereof ($C_7H_7$ for toluene) as a substituent bonded to another group, particularly other organic groups, containing both aliphatic and aromatic structures.

Binding or stable binding: An association between two substances or molecules, such as the association of a specific binding agent or moiety (e.g., antibody) with an antigen.

Binding affinity: The tendency of one molecule to bind (typically non-covalently) with another molecule, such as the tendency of a member of a specific binding pair for another member of a specific binding pair. A binding affinity can be measured as a binding constant, which binding affinity for a specific binding pair (such as an antibody/antigen pair or nucleic acid probe/nucleic acid sequence pair) can be at least $1\times10^5$ $M^{-1}$, such as at least $1\times10^6$ $M^{-1}$, at least $1\times10^7$ $M^{-1}$ or at least $1\times10^8$ $M^{-1}$. In one embodiment, binding affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity for an antibody/antigen pair is at least about $1\times10^8$ $M^{-1}$. In other embodiments, a high binding affinity is at least about $1.5\times10^8$ $M^{-1}$, at least about $2.0\times10^8$ $M^{-1}$, at least about $2.5\times10^8$ $M^{-1}$, at least about $3.0\times10^8$ $M^{-1}$, at least about $3.5\times10^8$ $M^{-1}$, at least about $4.0\times10^8$ $M^{-1}$, at least about $4.5\times10^8$ $M^{-1}$, or at least about $5.0\times10^8$ $M^{-1}$.

Chromogen: A substance capable of conversion to a colored product, such as a pigment or dye. Certain chromogens are electron donors that, when oxidized, become a colored product. Production of a colored product, and the property of becoming insoluble upon chemical conversion, such as by oxidation, make chromogens useful for IHC. Particular examples of chromogenic compounds, without limitation, include diaminobenzidine (DAB), tetramethylbenzidine (TMB), 2,2'-azino-di-[3-ethylbenzothiazoline sulphonate] (ABTS), iodonitrotetrazolium (INT), tetrazolium blue and tetrazolium violet.

DAB is a chromogen that produces a brown end product that is highly insoluble in alcohol and other organic solvents. In some examples, DAB is the substrate of an enzyme, such as HRP.

Conditions sufficient to detect: Any environment that permits the desired activity, for example, that permits a probe to bind a target and the interaction to be detected. For example, such conditions include appropriate temperatures, buffer solutions, and detection means such as microscopes and digital imaging equipment.

Contacting: Placement that allows association between two or more moieties, particularly direct physical association, for example both in solid form and/or in liquid form (for example, the placement of a biological sample, such as a biological sample affixed to a slide, in contact with a composition, such as a solution containing the compositions disclosed herein).

Control: A sample or procedure performed to assess test validity. In one example, a control is a quality control, such as a positive control. For example, a positive control is a procedure or sample, such as a tissue or cell, that is similar to the actual test sample, but which is known from previous experience to give a positive result. A positive control confirms that the basic conditions of the test produce a positive result, even if none of the actual test samples produce such result. In a particular example, a positive control is a sample known by previous testing to contain the suspected antigen.

In other examples, a control is a negative control. A negative control is a procedure or test sample known from previous experience to give a negative result. The negative control demonstrates the base-line result obtained when a test does not produce a measurable positive result; often the value of the negative control is treated as a "background" value to be subtracted from the test sample results. In a particular example, a negative control is a reagent that does not include the specific primary antibody. Other examples include calibrator controls, which are samples that contain a known amount of a control antigen. Such calibrator controls have an expected signal intensity, and therefore can be used to correct for inter- or intra-run staining variability.

Conjugate: A molecule comprising two independent molecules, which have been joined through a bond (typically a covalent or ionic bond). In some examples a specific binding agent or moiety is conjugated to an enzyme that acts on a substrate to produce a detectable moiety or label.

Conjugating, joining, bonding or linking: Joining one molecule to another molecule to make a larger molecule. For example, making two polypeptides into one contiguous polypeptide molecule, or covalently attaching a hapten or other molecule to a polypeptide, such as an scFv antibody. The linkage can be either by chemical or recombinant means. "Chemical means" refers to a reaction between the antibody moiety and the effector molecule such that there is a covalent bond formed between the two molecules to form one molecule.

Coupled: The term "coupled" means joined together, either directly or indirectly. A first atom or molecule can be directly coupled or indirectly coupled to a second atom or molecule. A secondary antibody provides an example of indirect coupling. One specific example of indirect coupling is a rabbit anti-hapten primary antibody that is bound by a mouse anti-rabbit IgG antibody, which is in turn bound by a goat anti-mouse IgG antibody that is covalently linked to a detectable label.

Derivative: In chemistry, a derivative is a compound that is derived from a similar compound or a compound that can be imagined to arise from another compound, for example, if one atom is replaced with another atom or group of atoms. The latter definition is common in organic chemistry. In biochemistry, the word is used for compounds that at least theoretically can be formed from the precursor compound.

Detectable Label: A molecule or material that can produce a detectable (such as visually, electronically or otherwise) signal that indicates the presence and/or concentration of a target, such as a target molecule, in a sample, such as a tissue sample. When conjugated to a specific binding molecule, the detectable label can be used to locate and/or quantify the target to which the specific binding molecule is directed. Thereby, the presence and/or concentration of the target in a sample can be detected by detecting the signal produced by the detectable label. A detectable label can be detected directly or indirectly, and several different detectable labels conjugated to different specific-binding molecules can be used in combination to detect one or more targets. For example, a first detectable label, such as a hapten conjugated to an antibody specific to a target, can be detected indirectly by using a second detectable label that is conjugated to a molecule that specifically binds the first detectable label. Multiple detectable labels that can be separately detected can be conjugated to different specific binding molecules that specifically bind different targets to provide a multiplexed assay that can provide detection of the multiple targets in a sample.

Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Particular examples of detectable labels include: enzymes, such as horseradish peroxidase, glucose oxidase, f3-galactosidase or β-glucuronidase; fluorphores (many additional examples of fluorescent molecules can be found in The Handbook—A Guide to Fluorescent Probes and Labeling Technologies, Molecular Probes, Eugene, Oreg.); nanoparticles, such as quantum dots (U.S. Pat. Nos. 6,815,064, 6,682,596 and 6,649,138, each of which patents is incorporated by reference herein); metal chelates, such as DOTA and DPTA chelates of radioactive or paramagnetic metal ions like $Gd^{3+}$; chromogens; and liposomes, for example, liposomes containing trapped fluorescent molecules.

Where the detectable label includes an enzyme, a detectable substrate such as a chromogen, a fluorogenic compound, or a luminogenic compound is used in combination with the enzyme to generate a detectable signal (a wide variety of such compounds are commercially available, for example, from Life Technologies, Carlsbad, Calif.).

Alternatively, an enzyme can be used in a metallographic detection scheme. Metallographic detection methods include using an enzyme in combination with a water-soluble metal ion and a redox-inactive substrate of the enzyme. The substrate is converted to a redox-active agent by the enzyme, and the redox-active agent reduces the metal ion, causing it to form a detectable precipitate. (See, for example, co-pending U.S. patent application Ser. No. 11/015,646, filed Dec. 20, 2004, PCT Publication No. 2005/003777 and U.S. Patent Application Publication No. 2004/0265922; each of which is incorporated by reference herein). Metallographic detection methods include using an oxidoreductase enzyme (such as horseradish peroxidase (HRP)) along with a water soluble metal ion, an oxidizing agent and a reducing agent, again to form a detectable precipitate (see, for example, U.S. Pat. No. 6,670,113, which is incorporated by reference herein).

Detergent or Surfactant: A substance that reduces the surface tension of water. Specifically, a detergent or surfactant is a surface-active agent, or surfactant, that concentrates at oil-water interfaces and exerts an emulsifying action. Detergents are classified as anionic, cationic, or nonionic, depending on their mode of chemical action. Nonionic detergents function via a hydrogen-bonding mechanism. Further, surfactants or detergents reduce interfacial tension between two liquids. A surfactant molecule typically has a polar or ionic "head" and a nonpolar hydrocarbon "tail." Upon dissolution in water, the surfactant molecules aggregate and form micelles, in which the nonpolar tails are oriented inward and the polar or ionic heads are oriented outward toward the aqueous environment. The nonpolar tails create a nonpolar "pocket" within the micelle. Nonpolar compounds in the solution are sequestered in the pockets formed by the surfactant molecules, thus allowing the nonpolar compounds to remain mixed within the aqueous solution.

Detect: To determine if an agent (such as a signal or particular antigen, protein or nucleic acid) is present or absent, for example, in a sample. In some examples, this can further include quantification, and/or localization, for example localization within a cell or particular cellular compartment. "Detecting" refers to any method of determining if something exists, or does not exist, such as determining if a target molecule is present in a biological sample. For example, "detecting" can include using a visual or a mechanical device to determine if a sample displays a specific characteristic. In certain examples, detection refers to visually observing a probe bound to a target, or observing that a probe does not bind to a target. For example, light microscopy and other microscopic means are commonly used to detect chromogenic precipitates for methods described here.

Electromagnetic radiation: A series of electromagnetic waves that are propagated by simultaneous periodic variations of electric and magnetic field intensity, and that includes radio waves, infrared, visible light, ultraviolet light, X-rays and gamma rays. In particular examples, electromagnetic radiation is emitted by a laser, which can possess properties of monochromaticity, directionality, coherence, polarization, and intensity.

Emission or emission signal: The light of a particular wavelength generated from a source. In particular examples, an emission signal is emitted from a fluorophore after the fluorophore absorbs light at its excitation wavelength(s).

Enhanc(e/er/ement/ing): An enhancer or enhancing reagent is any compound or any combination of compounds sufficient to increase the catalytic activity of an enzyme, as compared to the enzyme activity without such compound(s). Enhancer(s) or enhancing reagent(s) can also be defined as a compound or combination of compounds that increase or accelerate the rate of binding an activated conjugate to a receptor site.

Enhanc(e/ement/ing) is a process by which the catalytic activity of an enzyme is increased by an enhancer, as compared to a process that does not include such an enhancer. Enhanc(e/ement/ing) can also be defined as increasing or accelerating the rate of binding of an activated conjugate to a receptor site. Enhanc(e/ement/ing) can be measured visually, such as by scoring by a pathologist. In particular embodiments, scores range from greater than 0 to greater than 4, with the higher number indicating better visual detection. More typically, scores range from greater than 0 to about 4++, such as 1, 1.5, 2, 2.5, 3, 3.5, 3.75, 4, 4+, and 4++. In addition, enhanc(e/ement/ing) can be measured by determining the apparent $V_{max}$ of an enzyme. In particular embodiments, the term encompasses apparent $V_{max}$ values (measured as optical density/minute) ranging from greater than 0 mOD/min to about 400 mOD/min, such as about 15 mOD/min, 18 mOD/min, about 20 mOD/min, about 40 mOD/min, about 60 mOD/min, about 80 mOD/min, about 100 mOD/min, about 120 mOD/min, about 140 mOD/min, about 160 mOD/min, about 200 mOD/min, about 250 mOD/min, about 300 mOD/min, about 350 mOD/min, and about 400 mOD/min. More typically, the Vmax ranges from greater than 0 mOD/min to about 160 mOD/min, such as about 20 mOD/min, about 40 mOD/min, about 60 mOD/min, about 80 mOD/min, about 100 mOD/min, about 120 mOD/min, about 140 mOD/min, and about 160 mOD/min. In addition, enhancement can occur using any concentration of an enhancer greater than 0 mM. Typically, enhancement occurs at enhancer concentrations ranging from great than 0 mM to about 100 mM; even more typically from about 0.01 mM to about 100 mM, such as about 0.01 mM, about 0.02 mM, about 0.05 mM, about 0.10 mM, about 0.20 mM, about 0.50 mM, about 1.0 mM, about 2.0 mM, about 3.0 mM, about 5.0 mM, about 10.0 mM, about 20.0 mM, about 30.0 mM, about 40.0 mM, about 50.0 mM, about 75.0 mM, or about 100.0 mM, such as about 0.01 mM to about 0.10 mM, about 0.05 mM to about 0.50 mM, about 0.4 mM to about 1.0 mM, about 0.5 mM to about 2.0 mM, about 1.0 mM to about 10.0 mM, about 5.0 mM to about 50.0 mM, and about 20.0 mM to about 100.0 mM.

Excitation or excitation signal: The light of a particular wavelength necessary and/or sufficient to excite an electron transition to a higher energy level. In particular examples, an excitation is the light of a particular wavelength necessary and/or sufficient to excite a fluorophore to a state such that the fluorophore will emit a different (such as a longer) wavelength of light than the wavelength of light from the excitation signal.

Fixation: A process which preserves cells and tissue constituents in as close to a life-like state as possible and allows them to undergo preparative procedures without change. Fixation arrests the autolysis and bacterial decomposition processes that begin upon cell death, and stabilizes the cellular and tissue constituents so that they withstand the subsequent stages of tissue processing, such as for IHC.

Tissues may be fixed by either perfusion with or submersion in a fixative, such as an aldehyde (such as formaldehyde, paraformaldehyde, glutaraldehyde, and the like). Other fixatives include oxidizing agents (for example, metallic ions and complexes, such as osmium tetroxide and chromic acid), protein-denaturing agents (for example, acetic acid, methanol, and ethanol), fixatives of unknown mechanism (for example, mercuric chloride, acetone, and picric acid), combination reagents (for example, Carnoy's fixative, methacarn, Bouin's fluid, B5 fixative, Rossman's fluid, and Gendre's fluid), microwaves, and miscellaneous (for example, excluded volume fixation and vapour fixation). Additives also may be included in the fixative, such as buffers, detergents, tannic acid, phenol, metal salts (for example, zinc chloride, zinc sulfate, and lithium salts), and lanthanum.

The most commonly used fixative in preparing samples for IHC is formaldehyde, generally in the form of a formalin solution (4% formaldehyde in a buffer solution, referred to as 10% buffered formalin).

Fluorescence: A type of luminescence in which an atom or molecule absorbs energy and then emits visible light as it transitions from a higher to a lower electronic state. The term "fluorescence" is restricted to phenomena in which the time interval between absorption and emission of energy is extremely short.

Fluorescence in situ hybridization (FISH): FISH is a technique used to detect and localize the presence or absence of specific DNA and/or RNA sequences on chromosomes. FISH uses fluorescently labeled probes that bind to only those parts of the chromosome with which they show a high degree of sequence similarity under defined reaction conditions. FISH also can be used to detect particular mRNA sequences within tissue samples.

Fluorophore: A chemical compound, which when excited by exposure to a particular stimulus such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser. Examples of particular fluorophores that can be used in the probes disclosed herein are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (CIBACRON™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy5.

Hapten: A molecule, typically a small molecule that can combine specifically with an antibody, but typically is substantially incapable of being immunogenic except in combination with a carrier molecule. Examples of haptens include, but are not limited to fluorescein, biotin, nitroaryls, including, but, not limited to, dinitrophenol (DNP), digoxigenin, oxazole, pyrazole, thiazole, benzofuran, triperpene, urea, thiourea, rotenoid, coumarin and cycloligman.

Heterobifunctional: Cross-linking agents contain at least two different reactive groups at each end, which are reactive towards numerous groups, including but not limited to sulfhydryls and amines, and create chemical covalent bonds between two or more molecules, for example between specific binding agent or moiety (such as an antibody) and an enzyme (such as HRP).

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11).

Immunohistochemistry (IHC): A method of determining the presence or distribution of an antigen in a sample by detecting interaction of the antigen with a specific binding agent or moiety, such as an antibody. A sample including an antigen (such as a target antigen) is incubated with an antibody under conditions permitting antibody-antigen binding. Antibody-antigen binding can be detected by means of a detectable label conjugated to the antibody (direct detection) or by means of a detectable label conjugated to a secondary antibody, which is raised against the primary antibody (e.g., indirect detection). Detectable labels include, but are not limited to, radioactive isotopes, fluorochromes (such as fluorescein, fluorescein isothiocyanate, and rhodamine), enzymes and chromogenic molecules.

In situ hybridization (ISH): A type of hybridization that uses a labeled complementary DNA or RNA strand (i.e., probe) to localize a specific DNA or RNA sequence in a portion or section of tissue (in situ), or, if the tissue is small enough (e.g., plant seeds, *Drosophila* embryos), in the entire tissue (whole mount ISH). This is distinct from immunohistochemistry, which localizes proteins in tissue sections. DNA ISH can be used to determine the structure of chromosomes, such as for use in medical diagnostics to assess chromosomal integrity. RNA ISH (hybridization histochemistry) is used to measure and localize mRNAs and other transcripts within tissue sections or whole mounts.

For hybridization histochemistry, sample cells and tissues are usually treated to fix the target transcripts in place and to increase access of the probe to the target molecule. As noted above, the probe is either a labeled complementary DNA or a complementary RNA (Riboprobe). The probe hybridizes to the target sequence at elevated temperature, and then the excess probe is washed away (after prior hydrolysis using RNase in the case of unhybridized, excess RNA probe). Solution parameters, such as temperature, salt and/or detergent concentration, can be manipulated to remove any non-identical interactions (i.e. only exact sequence matches will remain bound). Then, the labeled probe having been labeled effectively, such as with either radio-, fluorescent- or antigen-labeled bases (e.g., digoxigenin), is localized and potentially quantitated in the tissue using either autoradiography, fluorescence microscopy or immunohistochemistry, respectively.

Linker: As used herein, a linker is a molecule or group of atoms positioned between two moieties. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker.

Linker peptide: A peptide within an antibody binding fragment (such as an Fv fragment) which serves to indirectly bond the variable heavy chain to the variable light chain. "Linker" can also refer to a peptide serving to link a targeting moiety, such as a scFv, to an effector molecule, such as a cytotoxin or a detectable label.

Molecule of interest or Target molecule: A molecule for which the presence, location and/or concentration is to be determined. Examples of molecules of interest include proteins and nucleic acid sequences present in tissue samples.

Multiplex, -ed, -ing: Embodiments of the present disclosure allow multiple targets in a sample to be detected substantially simultaneously, or sequentially, as desired, using plural different conjugates. Multiplexing can include identifying and/or quantifying nucleic acids generally, DNA, RNA, peptides, proteins, both individually and in any and all combinations. Multiplexing also can include detecting two or more of a gene, a messenger and a protein in a cell in its anatomic context.

Neoplasia and Tumor: The process of abnormal and uncontrolled cell growth. Neoplasia is one example of a proliferative disorder.

The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15, or 20 bases.

Probe: An isolated nucleic acid, an isolated synthetic oligonucleotide, attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In Molecular Cloning: A Laboratory Manual, CSHL, New York, 1989) and Ausubel et al. (In Current Protocols in Molecular Biology, Greene Publ. Assoc. and Wiley-Intersciences, 1992).

One of ordinary skill in the art will appreciate that the specificity of a particular probe increases with its length. Thus, probes can be selected to provide a desired specificity, and may comprise at least 17, 20, 23, 25, 30, 35, 40, 45, 50 or more consecutive nucleotides of desired nucleotide sequence. In particular examples, probes can be at least 100, 250, 500, 600 or 1000 consecutive nucleic acids of a desired nucleotide sequence.

Polypeptide: A polymer in which the monomers are amino acid residues that are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Sample: The term "sample" refers to any liquid, semi-solid or solid substance (or material) in or on which a target can be present. In particular, a sample can be a biological sample or a sample obtained from a biological material. Examples of biological samples include tissue samples and cytology samples. In some examples, the biological sample is obtained from an animal subject, such as a human subject. A biological sample is any solid or fluid sample obtained from, excreted by or secreted by any living organism, including without limitation, single celled organisms, such as bacteria, yeast, protozoans, and amebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample is a nuclear extract. In some examples, a biological sample is bacterial cytoplasm. In other examples, a sample is a test sample. For example, a test sample is a cell, a tissue or cell pellet section prepared from a biological sample obtained from a subject. In an example, the subject is one that is at risk or has acquired a particular condition or disease.

Specifically binds: A term that refers to the binding of agent that preferentially binds to a defined target (such as an antibody to a specific antigen or a nucleic acid probe to a specific nucleic acid sequence). With respect to an antigen, "specifically binds" refers to the preferential association of an antibody or other ligand, in whole or part, with a specific polypeptide. With respect to a nucleic acid sequence, "specifically binds" refers to the preferential association of a nucleic acid probe, in whole or part, with a specific nucleic acid sequence A specific binding agent or moiety binds substantially only to a defined target. It is recognized that a minor degree of non-specific interaction may occur between a molecule, such as a specific binding agent or moiety, and a non-target polypeptide or non-target nucleic acid sequence. Although a selectively reactive antibody binds an antigen, it can do so with low affinity. Antibody to antigen specific binding typically results in greater than 2-fold, such as greater than 5-fold, greater than 10-fold, or greater than 100-fold increase in amount of bound antibody or other ligand (per unit time) to a target polypeptide, as compared to a non-target polypeptide. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

Nucleic acid probe to nucleic acid sequence specific binding typically results in greater than 2-fold, such as greater than 5-fold, greater than 10-fold, or greater than 100-fold increase in amount of bound nucleic acid probe to a target nucleic acid sequence, as compared to a non-target nucleic acid. A variety of ISH conditions are appropriate for selecting nucleic acid probes that bind specifically with a particular nucleic acid sequence.

Specific binding moiety or Specific binding agent: A member of a specific-binding pair. Specific binding pairs are pairs of molecules that are characterized in that they bind each other to the substantial exclusion of binding to other molecules (for example, specific binding pairs can have a binding constant that is at least $10^3$ $M^{-1}$ greater, $10^4$ $M^{-1}$ greater or $10^5$ $M^{-1}$ greater than a binding constant for either of the two members of the binding pair with other molecules in a biological sample). Particular examples of specific binding moieties include specific binding proteins (for example, antibodies, lectins, avidins such as streptavidins, and protein A), nucleic acids sequences, and protein-nucleic acids. Specific binding moieties can also include the molecules (or portions thereof) that are specifically bound by such specific binding proteins.

Substrate: A molecule acted upon by a catalyst, such as an enzyme. In one example, a substrate is 4-Chloro-1-naphthol (4-CN), or diaminobenzidine (DAB).

Tissue: A collection of interconnected cells that perform a similar function within an organism.

Tyramine: A compound having the formula $C_8H_{11}NO$, also known as 4-(2-aminoethyl)phenol.

Tyramide: A tyramine derivative, wherein the amine functional group of a tyramine molecule has formed an amide bond with a carbonyl-containing functional group.

III. Overview of Several Embodiments

A. Compositions

Aspects of this disclosure relate to compositions that enhance the deposition of detectable moieties on tissue samples, for example tissue sections such as those being tested for the presence of markers, such as markers for disease. Thus, disclosed herein are compositions for enhancing deposition of detectable moieties on tissue samples, for example tissue sections. Enhanced deposition provides an improved ability to easily detect and identify targets in a tissue sample, for example by improving the quality, quantity and/or signal to noise ratio of detectable moieties on tissue samples. In certain embodiments, the disclosed compositions and methods provided herein increase and/or improve enzyme turnover by increasing the apparent enzyme oxidation rates, and thereby enhance the enzyme's ability to react with composition components and increase deposition of detectable moieties at the specific target site, such as the site of a target molecule in a sample. In such embodiments, the enzyme products are detectable moieties that are deposited on tissue samples. Exemplary composition components are further detailed in the following sections.

1. Enhancers

Disclosed embodiments utilize enhancers or enhancing solutions to improve enzyme activity towards deposition of detectable moieties, for example in the case of HRP by increasing the apparent enzyme reaction kinetics and thereby increasing the deposition rate of the enzyme substrate, such as the chromogenic reaction product of DAB and HRP. The disclosed enhancers can be used in solutions comprising other composition components, or they can comprise a separate solution, wherein the solution is separately added to other composition components. The solution can be an aqueous solution, a water-miscible organic solution, or any combination thereof. Exemplary organic solutions include, but are not limited to glycols, such as propylene glycol, dimethylsulfoxide, tetrahydrofuran, dimethylformamide, and any combination thereof.

i. Pyrimidine and Pyridine Analogs

Particular embodiments of the disclosed compositions include as enhancers pyrimidine analog and/or pyridine analogs having the following general formulas (Formula 1 and Formula 2):

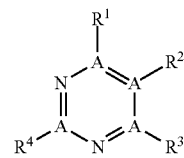

Formula 1

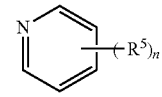

Formula 2

With reference to Formula 1, $R^1$, $R^2$, $R^3$, and $R^4$ independently can be aliphatic, aryl, halogen, a heteroatom-containing moiety, and hydrogen. In some examples, the halogen is iodine, bromine, chlorine, or fluorine. In some examples, the heteroatom-containing moiety is hydroxyl, ether, silyl ether, ester, carboxylic acid, silyl, phosphonate, phosphine, amide, or $NR^6R^7$ where $R^6$ and $R^7$ independently are hydrogen, aliphatic, aryl, heteroaliphatic, heteroaryl, or any combination thereof. In some examples, $R^1$ and/or $R^3$ are bound to $R^2$ to form a fused, ring system. In some examples, with reference to Formula 2 $R^5$ is a heteroatom-containing moiety, such as hydroxyl, ether, silyl ether, ester, carboxylic acid, silyl, phosphonate, phosphine, amide, or $NR^6R^7$ where $R^6$ and $R^7$ independently are hydrogen, aliphatic, aryl, heteroaliphatic, heteroaryl, or any combination thereof. With reference to Formula 1, in some examples, "A"

is a heteroatom (other than sulfur), a carbon atom, or any combination thereof. With reference to Formula 2, n is 1 to 5, such as 1, 2, 3, 4, or 5, for example 1-2, 2-3, 3-4, 4-5, 1-3, 2-4, 3-5, 1-4, 2-5, or 1-5. In specific examples, A is a carbon atom and n is 1. Exemplary pyrimidine analogs for inclusion in the disclosed compositions are pyrimidine and 2-hydroxypyrimidine and exemplary pyridine analogs are pyridine and 2-hydroxypyridine.

In some examples, enhancers are present in a solution, for example to facilitate dispensing from automated machines. In some examples, the enhancers are present in the solution at a concentration of about 0.01 mM to about 100 mM, such as about 0.01 mM, about 0.02 mM, about 0.05 mM, about 0.10 mM, about 0.20 mM, about 0.50 mM, about 1.0 mM, about 2.0 mM, about 3.0 mM, about 5.0 mM, about 10.0 mM, about 20.0 mM, about 30.0 mM, about 40.0 mM, about 50.0 mM, about 75.0 mM, or about 100.0 mM, such as about 0.01 mM to about 0.10 mM, about 0.05 mM to about 0.50 mM, about 0.4 mM to about 1.0 mM, about 0.5 mM to about 2.0 mM, about 1.0 mM to about 10.0 mM, about 5.0 mM to about 50.0 mM, and about 20.0 mM to about 100.0 mM.

ii. Optional Enhancers

In particular embodiments, the pyrimidine and pyridine analog enhancers are used in conjunction with additional optional enhancers. In some embodiments, the optional enhancers are included in the same solution as the pyrimidine and pyridine analog enhancers, and thus can be contacted to a tissue sample as a single composition, such as a single solution. In some instances it might be desirable to include the optional enhancers in a separate solution, for example to avoid reactivity and/or reduced solubility. Thus, in some embodiments, the optional enhancers are included in a different solution from the pyrimidine and pyridine analog enhancers, and thus can be contacted to a tissue sample from a separate solution, for example as stepwise delivery or simultaneous delivery.

Particular embodiments of the disclosed compositions contain optional enhancers that may or may not be used in combination with the pyrimidine analog and/or the pyridine analog, depending on such factors as the particular application or detectable moieties or enzymes, amongst others. In particular embodiments, a disclosed composition contains, as optional enhancers, heteroaryl enhancers having the following general formula (Formula 3):

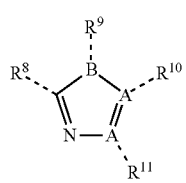

Formula 3

With reference to Formula 3, $R^8$, $R^9$, $R^{10}$ and $R^{11}$ independently are aliphatic, aryl, halogen, a heteroatom-containing moiety, hydrogen, or any combination thereof. In certain examples, the halogen is iodine, bromine, chlorine or fluorine. In certain examples, the heteroatom-containing moiety is hydroxyl, ether, silyl ether, ester, carboxylic acid, silyl, phosphonate, phosphine, amide, or $NR^6R^7$ where $R^6$ and $R^7$ independently are hydrogen, aliphatic, aryl, heteroaliphatic, heteroaryl, or any combination thereof. With reference to Formula 3, "A" is a heteroatom (other than sulfur) a carbon atom, or any combination thereof. With reference to Formula 3, "B" is oxygen, carbon, or nitrogen. In specific examples, A is a carbon atom and B is a nitrogen atom. In certain embodiments, heteroaryl enhancers for use in the disclosed compositions are selected from imidazole, L-histidine, thiazole, oxazole, or any combination thereof. In some examples, enhancers are present in a solution, for example to facilitate dispensing from automated machines.

In some embodiments, the disclosed compositions contain, as optional enhancers, heteroaryl enhancers having the following general formulas (Formula 4 and Formula 5):

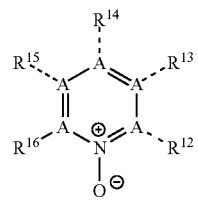

Formula 4

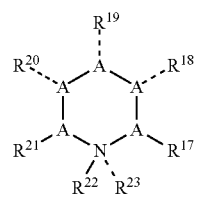

Formula 5

With reference to Formulas 4 and 5, $R^{12}$-$R^{23}$ independently are aliphatic, aryl, halogen, a heteroatom-containing moiety, hydrogen, or any combination thereof. In some examples, the halogen moiety is iodine, bromine, chlorine or fluorine. In some examples, the heteroatom-containing moiety is hydroxyl, ether, silyl ether, ester, carboxylic acid, silyl, phosphonate, phosphine, amide, or $NR^6R^7$ where $R^6$ and $R^7$ independently are hydrogen, aliphatic, aryl, heteroaliphatic, heteroaryl, or any combination thereof. In certain embodiments, $R^{22}$ is a radical species, such as [O]., or a negatively-charged species, such as [O]$^-$. With reference to Formula 5, in particular embodiments, $R^{21}$ and $R^{17}$ comprise a geminal di-methyl group. With reference to Formula 5 and/or 6 "A" is a heteroatom (other than sulfur), a carbon atom, or any combination thereof. In specific examples, A is a nitrogen atom, an oxygen atom, a carbon atom, or any combination thereof. In specific embodiments, heteroaryl enhancers include, but are not limited to, pyrimidine N-oxide, pyridine N-oxide, N-methyl morpholine (NMO), and 2,2,6,6-tetramethylpiperidine-1-oxyl (TEMPO).

In some embodiments the disclosed compositions contain, as optional enhancers, organic and inorganic boronic acids. In some embodiments, organic boronic acids have the following general formula (Formula 6):

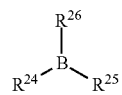

Formula 6

With reference to Formula 6, $R^{24}$, $R^{25}$, and $R^{26}$ independently are aliphatic, aryl, heteroaliphatic, heteroaryl, or any combination thereof. In specific examples, two or more, such as 2 or 3, of $R^{24}$, $R^{25}$, and $R^{26}$ are hydroxyl, with the remaining $R^{24}$, $R^{25}$, or $R^{26}$ being aliphatic, aryl, heteroaliphatic, or heteroaryl. In particular embodiments, $R^{24}$, $R^{25}$, and $R^{26}$ independently are alkyl, alkenyl, alkynyl, and phenyl. In certain embodiments of the disclosed composition, organic boronic acids are boric acid, phenyl boronic acid, 4-AcHN-phenyl boronic acid, or any combination thereof.

In some embodiments, the disclosed compositions include phenolic compounds as optional enhancers. In some embodiments, phenolic compounds have the following general formula (Formula 7):

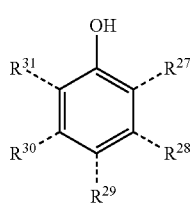

Formula 7

With reference to Formula 7, $R^{27}$, $R^{28}$, $R^{29}$, $R^{30}$, and $R^{31}$ independently are hydrogen, aliphatic, aryl, a heteroatom-containing moiety, halogen, or any combination thereof. In some examples, the halogen moiety is iodine, bromine, chlorine or fluorine. In some examples, the heteroatom-containing moiety is hydroxyl, ether, silyl ether, ester, carboxylic acid, silyl, phosphonate, phosphine, amide, or $NR^6R^7$ where $R^6$ and $R^7$ independently are hydrogen, aliphatic, aryl, heteroaliphatic, heteroaryl, or any combination thereof. In particular embodiments, any two adjacent groups selected from $R^{27}$, $R^{28}$, $R^{29}$, $R^{30}$, and $R^{31}$ can be bound to form a fused, aromatic or non-aromatic ring system. In additional particular embodiments, at least one of $R^{27}$, $R^{28}$, $R^{29}$, $R^{30}$ and $R^{31}$ is selected from hydroxyl. Particular working embodiments concern phenolic compounds as optional enhancers, such as pyrocatechol.

2. Detectable Moieties

The disclosed compositions allow for increased detection of detectable moieties. These detectable moieties can be selected from any moiety that is capable of being used with tissue samples. Particular embodiments employ detectable moieties selected from chromogens, fluorophores, tyramide conjugates, which are formed between tyramine and haptens, nanoparticles, fluorophores, and proteins, or any combination thereof.

Particular embodiments utilize chromogens as detectable moieties. Chromogens can be selected from any compound capable of producing a detectable color change upon deposition on tissue, for example a tissue sample such as a tissue section typically employed for pathology examination. In some examples, the detectable moiety is deposited in sample tissue after it has been acted on by an enzyme. By way of example, the enzyme is targeted to a target molecule in a tissue sample, the enzyme acts upon the detectable moiety, which in turn is deposited in on the sample in the immediate proximity of the enzyme, thus enabling the detection, quantification and/or localization of the target molecule in a tissue sample. The detectable moieties can be used in solutions comprising other composition components, or they can comprise a separate solution, wherein the solution is separately added to other composition components. Specific binding moieties can be designed to be directly conjugated to a label. Used in this way the specific binding/label complex (i.e., the probe) is contacted with the sample and the target is detected.

Specific binding moieties can also be indirectly associated with a label. In some examples, a first specific binding moiety is contacted with a sample. The specific binding moieties can be either nucleic acid based or protein based. The specific binding moiety can be conjugated to another moiety that is then bound for instance by a secondary antibody or a non-peptide based binding moiety, such as biotin. The secondary antibody or non-peptide binding pair can then be linked to a label, such as an enzyme. In another example, a specific binding moiety can be indirectly associated with a label by conjugating the specific binding moiety, either directly or indirectly, to a peptide having enzymatic activity. The enzymatic activity is chosen so that upon addition of a substrate(s), the substrate(s) is converted into a detectable moiety, or becomes a more active label.

Exemplary non-limiting examples of enzyme/substrate pairs include the following: HRP/DAB with a chromogenic substrate or fluorogenic substrate. Numerous other enzyme-substrate combinations are known to those skilled in the art. For a general review of these, see U.S. Pat. Nos. 4,275,149, and 4,318,980. When a probe is made from the indirect association of one or more additional molecules, the additional molecules can be referred to as probe components.

In some examples, the label is indirectly conjugated with an antibody. For example, an antibody can be conjugated to biotin wherein biotin binds selectively to avidin for subsequent detection. Alternatively, an antibody is conjugated with a small hapten and a label is conjugated to an anti-hapten antibody. Thus, indirect conjugation of the label with the targeting moiety can be achieved.

When the probe includes an enzyme that reacts with a substrate to generate the detection label, the substrate can be a chromogenic compound. There are numerous examples of such substrates. For example, many such compounds can be purchased from Invitrogen, Eugene Oreg. Particular non-limiting examples of chromogenic compounds include nitrophenyl-β-D-galactopyranoside (ONPG), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethylcarbazol (AEC), 10-acetyl-3,7-dihydroxyphenoxazine (ADHP), diaminobenzidine (DAB), tetramethylbenzidine (TMB), 2,2'-azino-di-[3-ethylbenzothiazoline sulphonate] (ABTS), o-dianisidine, 4-chloronaphthol (4-CN) (used in conjunction with DMPDA/DEPDA/MBTH/ADET, according to Kidwell, et al. *Anal. Biochem*., (1991), 192, 207), and o-phenylenediamine (OPD).

Particular embodiments utilize fluorophores as detectable moieties. Fluorophores can be selected from compounds that exhibit fluorescence, including, but not limited to, fluoresceins, luminophores, coumarins, BODIPY dyes, resorufins, and rhodamines. Examples of particular fluorophores that can be used in the probes disclosed herein are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (CIBACRON™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy5 (many additional examples of fluorescent molecules can be found in *The Handbook—A Guide to Fluorescent Probes and Labeling Technologies*, Molecular Probes, Eugene, Oreg., which is incorporated by reference herein).

In other embodiments, the detectable moiety can comprise a tyramide conjugate comprising a tyramine compound conjugated to a detectable moiety selected from nanoparticles, fluorophores, and proteins. Certain embodiments use tyramide conjugates comprising tyramine and a hapten wherein the hapten is selected from oxazole, pyrazole, thiazole, benzofurazan, triterpene, urea, thiourea, nitroaryl, rotenoid, coumarin, cyclolignan, heterobiaryl, azoaryl, benzodiazepine, or combinations thereof.

Other embodiments contemplated by the present disclosure include tyramide conjugates that include a tyramine compound bound to a nanoparticle, such as a quantum dot. Other particular embodiments include a tyramine compound bound to a fluorophore, which can be selected from fluoresceins, luminophores, coumarins, BODIPY dyes, resorufins, and rhodamines. Yet other particular embodiments concern a tyramine compound bound to a protein, which can be selected from an enzyme, such as horseradish peroxidase, glucose oxidase, β-galactosidase, β-glucuronidase or β-lactamase.

In particular embodiments, the detectable label or hapten is attached to the tyramine compound via a linker, such as an aliphatic linker, a heteroaliphatic linker, or any other flexible attachment moiety with comparable reactivities. For example, a tyramine compound can be covalently modified with a detectable label via a heterobifunctional polyalkyleneglycol linker such as a heterobifunctional polyethyleneglycol (PEG) linker.

One class of linkers suitable for forming disclosed tyramine-detectable moiety conjugates and tyramide-hapten conjugates are aliphatic compounds, such as aliphatic hydrocarbon chains having one or more sites of unsaturation, or alkyl chains. The aliphatic chain also typically includes terminal functional groups, including by way of example and without limitation, a carbonyl-reactive group, an amine-reactive group, a thiol-reactive group or a photo-reactive group, that facilitate coupling to detectable moieties and other desired compounds. The length of the chain can vary, but typically has an upper practical limit of about 30 atoms. Chain links greater than about 30 carbon atoms have proved to be less effective than compounds having smaller chain links. Thus, aliphatic chain linkers typically have a chain length of from about 1 carbon atom to about 30 carbon atoms. However, a person of ordinary skill in the art will appreciate that, if a particular linker has greater than 30 atoms, and still operates efficiently for linking the detectable moiety to a tyramine compound, and the conjugate still functions as desired, then such chain links are still within the scope of the present invention. Typical concentrations for tyramide-hapten conjugates comprising the disclosed linkers range from about 500 µM to about 100 µM. Even more typical concentrations range from about 5 µM to about 55 µM.

Another class of linkers useful are alkylene oxides. The alkylene oxides are represented herein by reference to glycols, such as ethylene glycols. A person of ordinary skill in the art will appreciate that, as the number of oxygen atoms increases, the hydrophilicity of the compound also may increase. Thus, linkers of the present disclosure typically have a formula of $(-OCH_2CH_2O-)_n$, where n is from about 2 to about 15, but more particularly is from about 2 to about 8. In some examples, the detectable moieties are present in the solution at a concentration of about 0.01 mM to about 10.0 mM, such as about 0.01 mM, about 0.02 mM, about 0.05 mM, about 0.10 mM, about 0.20 mM, about 0.50 mM, about 1.0 mM, about 2.0 mM, about 3.0 mM, about 5.0 mM, or about 10.0 mM, such as about 0.01 mM to about 0.10 mM, about 0.05 mM to about 0.50 mM, about 0.4 mM to about 1.0 mM, about 0.5 mM to about 2.0 mM, and about 1.0 mM to about 10.0 mM.

3. Specific Binding Moiety Conjugates

Particular embodiments concern using conjugates comprising a specific binding moiety and an enzyme, wherein the specific binding moiety is capable of recognizing and binding to a particular target in a sample. Specific binding moieties can be selected from oligonucleotides, nucleic acids, proteins, and peptides. Particular embodiments concern using proteins, such as antibodies, as specific binding moieties.

In particular embodiments, the specific binding moiety is bound to an enzyme. Examples of enzymes contemplated of the method can include oxidoreductases, such as peroxidases. Particular embodiments concern using horseradish peroxidase, glutathione peroxidase or any other peroxidase containing a heme moiety.

In certain embodiments, conjugates comprising a specific binding moiety and a hapten can be used in conjunction with a second conjugate comprising an anti-hapten antibody and an enzyme. In these particular embodiments, the specific binding moiety, typically an antibody, can recognize a target in a sample and bind thereto. The specific binding moiety is bound to a hapten, which will be recognized by the second conjugate comprising the anti-hapten antibody and an enzyme. This second antibody conjugate will bind with the first conjugate, thereby binding the enzyme to the target. The hapten can be selected from oxazole, pyrazole, thiazole, benzofurazan, triterpene, urea, thiourea, nitroaryl, rotenoid, coumarin, cyclolignan, heterobiaryl, azoaryl, benzodiazepine, or combinations thereof. Exemplary antibodies include, but are not limited to, rabbit IgG, mouse IgG, mouse IgM, and goat IgG. Exemplary enzymes are as previously disclosed. In some examples, the specific binding moiety and an enzyme conjugates are present in the solution at a concentration of about 0.01 mM to about 10.0 mM, such as about 0.01 mM, about 0.02 mM, about 0.05 mM, about 0.10 mM, about 0.20 mM, about 0.50 mM, about 1.0 mM, about 2.0 mM, about 3.0 mM, about 5.0 mM, or about 10.0 mM, such as about 0.01 to about 0.10, about 0.05 to about 0.50, about 0.4 to about 1.0, about 0.5 to about 2.0, and about 1.0 to about 10.0.

4. Other Components

Particular embodiments concern compositions further comprising Group I or Group II metal-containing salts having a formula MX. or MX, were M is a Group I or Group II metal, and X is selected from halide, such as fluoride, bromide, chloride, and iodide; and oxygen-containing ions, such as carbonate, hydroxide, and phosphate. Particular embodiments concern using Group I metal selected from sodium, lithium, cesium, and potassium. Other particular embodiments concern using Group II metals selected from magnesium, calcium, strontium, and barium. Particular embodiments utilize calcium and/or magnesium salt enhancers selected from calcium chloride, magnesium chloride, and calcium carbonate. In some examples, the optional enhancers are present in the solution at a concentration of about 0.01 mM to about 100 mM, such as about 0.01 mM, about 0.02 mM, about 0.05 mM, about 0.10 mM, about 0.20 mM, about 0.50 mM, about 1.0 mM, about 2.0 mM, about 3.0 mM, about 5.0 mM, about 10.0 mM, about 20.0 mM, about 30.0 mM, about 40.0 mM, about 50.0 mM, about 75.0 mM, or about 100.0 mM, such as about 0.01 mM to about 0.10 mM, about 0.05 mM to about 0.50 mM, about 0.4 mM to about 1.0 mM, about 0.5 mM to about 2.0 mM, about 1.0 mM to about 10.0 mM, about 5.0 mM to about 50.0 mM, and about 20.0 mM to about 100.0 mM.

Particular embodiments concern compositions further comprising oxidants, inhibitors, and surfactants as components that can be used in any combination with any of the previously disclosed components. Oxidants can include any compound capable of effectively activating the enzyme. Particular embodiments concern using peroxides, such as hydrogen peroxide, as oxidants used for activating the enzyme. Typically, the oxidant is 0.03% hydrogen peroxide.

An inhibitor can be selected from any compound capable of effectively inhibiting the enzyme after it has sufficiently reacted in a manner that results in deposition of the detectable moiety. Particular embodiments concern inhibitors selected from peroxidases. Typically, hydrogen peroxide is used as an inhibitor. Certain embodiments concern using 3% hydrogen peroxide as an inhibitor. In particular embodiments, the inhibitor is added to the sample subsequent to addition of the other composition components.

Particular embodiments of this disclosure concern compositions for use in detecting a target molecule in a sample, such as a tissue sample. In some embodiments, commercially viable compositions comprise a pyrimidine analog and/or a pyridine analog, an optional enhancer, a detectable moiety, a specific binding moiety conjugate, an enzyme, an oxidant, and a surfactant. These composition components can be added in any order and any combination that results in effectively depositing the detectable moiety at the target in the sample. The compositions can be used in conjunction with a second antibody, which is conjugated to an enzyme, an oxidant, and a dye.

In particular working embodiments, the pyrimidine analog and/or pyridine analog is selected from 2-hydroxypyrimidine and/or 2-hydroxypyridine. In particular working embodiments, the specific binding moiety conjugate is a haptenated IgG antibody conjugate and the secondary antibody comprises an anti-hapten multimer HRP conjugate.

Particular disclosed embodiments concern using a surfactant. Surfactants are classified as anionic, cationic, or nonionic, depending on their mode of chemical action. Nonionic surfactants function via a hydrogen-bonding mechanism. Further, surfactants reduce interfacial tension between two liquids. A surfactant molecule typically has a polar or ionic "head" and a nonpolar hydrocarbon "tail." Upon dissolution in water, the surfactant molecules aggregate and form micelles, in which the nonpolar tails are oriented inward and the polar or ionic heads are oriented outward toward the aqueous environment. The nonpolar tails create a nonpolar "pocket" within the micelle. Nonpolar compounds in the solution are sequestered in the pockets formed by the surfactant molecules, thus allowing the nonpolar compounds to remain mixed within the aqueous solution. In particular disclosed embodiments, the surfactant may be used to produce uniform spreading of reagents across a tissue section as well as decrease background staining.

Examples of surfactants include, but are not limited to polyoxyethylene alkyl ether, wherein the alkyl is $(CH_2)_M$ and the oxyethylene is $(C_2H_4O)_N$, wherein M is an integer from 5 to 16, from 8 to 14, or from 10 to 12 and N is an integer from 10 to 40, from 15 to 30, or from 20 to 28. In one embodiment, the surfactant is polyoxyethylene lauryl ether having a formula $(C_2H_{4O})_{23}C_{12}H_{25}OH$. In another embodiment, the surfactant is a polyoxyethylene (20) sorbitan monoalkylate, the monoalkylate comprising between 8 and 14 carbons. In another embodiment, the surfactant is a linear secondary alcohol polyoxyethylene having a formula $C_{12-14}H_{25-29}O(CH_2CH_2O]_x$, wherein x equals an integer between 2 and 12. In yet another embodiment, the surfactant is a polyoxyethylene octyl phenyl ether. Exemplary surfactants are sold under the names: Brij® 35, TWEEN®, Tergitol™, Triton™, Ecosurf™, Dowfax™ polysorbate 80™, BigCHAP, Deoxy BigCHAP, IGEPAL®, Saponin, Thesit®, Nonidet®, Pluronic F-68, digitonin, deoxycholate, and the like. Particular disclosed working embodiments concern using surfactants selected from Brij® 35, TWEEN®, Tergitol™, Triton™.

B. Method of Detecting a Target Molecule

The disclosed compositions are particularly useful for the detection of target molecules in samples because they act synergistically to provide maximized deposition during IHC or ISH tissue staining. Thus, the present disclosure provides a method of detecting a target molecule in a sample, such as a tissue sample. In some embodiments, the method includes contacting a sample with an enhancing solution that includes a pyrimidine analog and/or a pyridine analog as described in the preceding section (Section A), contacting the sample with an enzyme and contacting the sample with a detectable moiety capable of being detected using deposition or fluorescent techniques. In some examples, the enzyme acts on a substrate to catalyze the production of the detectable moiety, which is deposited on the sample at the location of the target molecule, thus enabling the detection of the target molecule. The detectable moiety is detected, thereby detecting the target molecule in a sample. In some examples, the intensity and/or location of a signal produced by the detectable moiety is measured, for example to determine the amount and/or the location of the target molecule in the tissue sample. The target can be any molecule of interest for which the presence, location and/or concentration is to be determined. Examples of molecules of interest include proteins and nucleic acid sequences. In some embodiments, the pyrimidine analog is pyrimidine and/or 2-hydroxypyrimidine. In some embodiments, the pyridine analog is 2-hydroxypyridine.

In some embodiments, the enzyme is immobilized on the target by incubating the sample with an enzyme conjugate that binds to the target. The enzyme may be conjugated to any moiety capable of binding to the target, for example conjugated to an antibody or nucleic acid that specifically recognizes the target molecule. Suitable moieties include, but are not limited to, antibodies, nucleotides, oligonucleotides, proteins, peptides, or amino acids.

In other embodiments, immobilizing the enzyme is a multi-step process. For example, the sample may be incubated with a first moiety (e.g., an antibody, nucleotide, oligonucleotide, protein, oligopeptide, peptide, or amino acid) that binds to the target. The sample then may be incubated with an enzyme conjugate comprising a moiety that is capable of binding to the first moiety. In some embodiments, where the first moiety is an antibody to the target, the two-step process may be more versatile because it allows the user to employ a "universal" enzyme-antibody conjugate. For example, if the first antibody is a rabbit monoclonal antibody, the enzyme-antibody conjugate may include an antibody that is capable of binding to any rabbit monoclonal antibody, for example a secondary antibody. The multi-step process can eliminate the need to generate an enzyme-antibody conjugate that is suitable for each target.

In some embodiments, the first moiety may be a labeled probe, such as a labeled oligonucleotide. After the probe has been hybridized to the sample, a first antibody that recognizes the label is introduced and binds to the labeled probe. The first antibody may be an enzyme-antibody conjugate. However, if the first antibody is not conjugated to an enzyme, an enzyme-antibody conjugate is introduced wherein the antibody moiety of the conjugate recognizes and binds to the first antibody.

In some embodiments, the enzyme is a peroxidase, such as horseradish peroxidase or glutathione peroxidase or an oxidoreductase. Thus, suitable conditions are selected for enzyme reaction such as a salt concentration and pH that enable the enzyme to perform its desired function, for example to convert the substrate to a detectable moiety that is deposited on the tissue sample at the site of the target molecule. The reaction is performed at a temperature that is suitable for the enzyme. For example, if the enzyme is horseradish peroxidase, the reaction may be performed at about 35-40° C.

In some examples, a detectable moiety is a chromogen, a fluorophore, a hapten, or a protein. In specific examples, the detectable moiety is 1,3-diaminobenzidine, 3-amino-9-ethylcarbazole, or tetramethylbenzidine, or a reaction product thereof. Additional examples of chromogens for use in the disclosed methods are given in the preceding section (Section A).

In other examples, a detectable moiety is a fluorophore, such as a fluorescein, a luminophore, a coumarin, a BODIPY dye, a resorufin, or a rhodamine. Additional examples of fluorophores for use in the embodiments of the disclosed method are given in the preceding section (Section A).

In other examples, a detectable moiety is a hapten, such as an oxazole, a pyrazole, a thiazole, a benzofurazan, a triterpene, a urea, a thiourea, a nitroaryl, a rotenoid, a coumarin, a cyclolignan, a heterobiaryl, an azoaryl, or benzodiazepine.

In specific embodiments, the detectable moiety is conjugated to tyramine, for example via a linker, such as an aliphatic, or heteroaliphatic linker from about 1 to about 30 carbon atoms in a chain. In specific embodiments, the linker is an alkylene oxide, such as ethylene glycol or a polymer thereof, for example a polymer with from 1 to about 15 ethylene glycol units. When tyramines are used with the disclosed methods, tyramide signal amplification can be used to further amplify the signal generated. Tyramide signal amplification utilizes the catalytic activity of a peroxidase enzyme to covalently bind a tyramine, or tyramine derivative, residue to a solid phase. The solid phase may be, for example, protein components of cells or cellular structures that are immobilized on a substrate such as a microscope slide. Some peroxidase enzymes (e.g., horseradish peroxidase), in the presence of a peroxide, can catalyze the dimerization of phenolic compounds. Thus, if tyramine is added to a protein-containing sample in the presence of horseradish peroxidase and peroxide (e.g., hydrogen peroxide), the tyramine phenol group can form a dimer with the phenol group of a tyrosine amino acid.

Only tyramine molecules in close proximity to the immobilized enzyme will react and form dimers with tyrosine residues in the vicinity of, or proximal to, the immobilized enzyme, including tyrosine residues in the enzyme itself, tyrosine residues in the antibody to which the enzyme is conjugated, and/or tyrosine residues in the sample that are proximal the immobilized enzyme, such as within about 100 nm, within about 50 nm, within about 10 nm, or within about 5 nm of the immobilized enzyme. For example, the tyrosine residue may be within a distance of about 10 angstroms to about 100 nm, about 10 angstroms to about 50 nm, about 10 angstroms to about 10 nm, or about 10 angstroms to about 5 nm from the immobilized enzyme. Such proximal binding allows the target to be detected with at least the same degree of specificity as conventional staining methods used with IHC and/or ISH. For example, embodiments of the disclosed method allow sub cellular structures to be distinguished, e.g., nuclear membrane versus the nuclear region, cellular membrane versus the cytoplasmic region, etc.

Once the enzyme is immobilized on the sample, the tyramide conjugate is introduced under suitable conditions to enable the enzyme to react with the tyramide. Typically the enzyme is a peroxidase, such as horseradish peroxidase. Under such conditions, the tyramide reacts with the peroxide and the enzyme, converting the tyramide to an active form that covalently binds to the sample, typically by binding to a tyrosine residue proximal to the immobilized enzyme, including tyrosine residues within the immobilized enzyme itself. After the tyramide conjugate is bound to the sample, its presence is detected by suitable means, for example by virtue of a detectable moiety linked to the tyramide.

In some embodiments, the sample is further contacted with at least one optional enhancer, such as one or more of a heteroaryl compound, a Group I or Group II metal-containing salt, a boron-containing compound, a phenol compound. Exemplary optional enhancers are described in the preceding section (Section A). In some embodiments, the sample is further contacted with an oxidant, such as a peroxidase, for example hydrogen peroxidase. In some embodiments, the sample is further contacted with a surfactant, such as Brij® 35, TWEEN®, Tergitol™, and Triton™. In some embodiments, the sample is further contacted with an antioxidant, such as sodium stannate, sodium metabisulfate, and sodium bisulfate.

The embodiments of the method as disclosed herein can be performed manually or automatically, for example on an automated tissue processing instrument. Automated systems typically are at least partially, if not substantially entirely, under computer control. Because automated systems typically are at least partially computer controlled, certain embodiments of the present disclosure also concern one or more tangible computer-readable media that stores computer-executable instructions for causing a computer to perform disclosed embodiments of the method.

C. Samples and Targets

Samples include biological components and generally are suspected of including one or more target molecules of interest. Target molecules can be on the surface of cells and the cells can be in a suspension, or in a tissue section. Target molecules can also be intracellular and detected upon cell lysis or penetration of the cell by a probe. One of ordinary skill in the art will appreciate that the method of detecting target molecules in a sample will vary depending upon the type of sample and probe being used. Methods of collecting and preparing samples are known in the art.

Samples for use in the embodiments of the method and with the composition disclosed herein, such as a tissue or other biological sample, can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Such normal samples are useful, among other things, as controls for comparison to other samples. The samples can be analyzed for many different purposes. For example, the samples can be used in a scientific study or for the diagnosis of a suspected malady, or as prognostic indicators for treatment success, survival, etc.

Samples can include multiple targets that can be specifically bound by a probe or reporter molecule. The targets can be nucleic acid sequences or proteins. Throughout this disclosure when reference is made to a target protein it is understood that the nucleic acid sequences associated with that protein can also be used as a target. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

A target nucleic acid sequence can vary substantially in size. Without limitation, the nucleic acid sequence can have a variable number of nucleic acid residues. For example a target nucleic acid sequence can have at least about 10 nucleic acid residues, or at least about 20, 30, 50, 100, 150, 500, 1000 residues. Similarly, a target polypeptide can vary substantially in size. Without limitation, the target polypeptide will include at least one epitope that binds to a peptide specific antibody, or fragment thereof. In some embodiments that polypeptide can include at least two epitopes that bind to a peptide specific antibody, or fragment thereof.

In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, at least a portion of the target molecule is produced by a nucleic acid sequence (e.g., genomic target nucleic acid sequence) amplified or deleted in at least a subset of cells in a sample.

Oncogenes are known to be responsible for several human malignancies. For example, chromosomal rearrangements involving the SYT gene located in the breakpoint region of chromosome 18q11.2 are common among synovial sarcoma soft tissue tumors. The t(18q11.2) translocation can be identified, for example, using probes with different labels: the first probe includes FPC nucleic acid molecules generated from a target nucleic acid sequence that extends distally from the SYT gene, and the second probe includes FPC nucleic acid generated from a target nucleic acid sequence that extends 3' or proximal to the SYT gene. When probes corresponding to these target nucleic acid sequences (e.g., genomic target nucleic acid sequences) are used in an in situ hybridization procedure, normal cells, which lack a t(18q11.2) in the SYT gene region, exhibit two fusion (generated by the two labels in close proximity) signals, reflecting the two intact copies of SYT. Abnormal cells with a t(18q11.2) exhibit a single fusion signal.

In other examples, a target protein produced from a nucleic acid sequence (e.g., genomic target nucleic acid sequence) is selected that is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX GLTSCR2, and GLTSCR1) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC_000007, nucleotides 55054219-55242525), the C-MYC gene (8q24.21; e.g., GENBANK™ Accession No. NC_000008, nucleotides 128817498-128822856), D5S271 (5p15.2), lipoprotein lipase (LPL) gene (8p22; e.g., GENBANK™ Accession No. NC_000008, nucleotides 19841058-19869049), RB1 (13q14; e.g., GENBANK™ Accession No. NC_000013, nucleotides 47775912-47954023), p53 (17p13.1; e.g., GENBANK™ Accession No. NC_000017, complement, nucleotides 7512464-7531642)), N-MYC (2p24; e.g., GENBANK™ Accession No. NC_000002, complement, nucleotides 151835231-151854620), CHOP (12q13; e.g., GENBANK™ Accession No. NC_000012, complement, nucleotides 56196638-56200567), FUS (16p11.2; e.g., GENBANK™ Accession No. NC_000016, nucleotides 31098954-31110601), FKHR (13p14; e.g., GENBANK™ Accession No. NC_000013, complement, nucleotides 40027817-40138734), as well as, for example: ALK (2p23; e.g., GENBANK™ Accession No. NC_000002, complement, nucleotides 29269144-29997936), Ig heavy chain, CCND1 (11q13; e.g., GENBANK™ Accession No. NC_000011, nucleotides 69165054, 69178423), BCL2

(18q21.3; e.g., GENBANK™ Accession No. NC_000018, complement, nucleotides 58941559-59137593), BCL6 (3q27; e.g., GENBANK™ Accession No. NC_000003, complement, nucleotides 188921859-188946169), MALF1, AP1 (1p32-p31; e.g., GENBANK™ Accession No. NC_000001, complement, nucleotides 59019051-59022373), TOP2A (17q21-q22; e.g., GENBANK™ Accession No. NC_000017, complement, nucleotides 35798321-35827695), TMPRSS (21q22.3; e.g., GENBANK™ Accession No. NC_000021, complement, nucleotides 41758351-41801948), ERG (21q22.3; e.g., GENBANK™ Accession No. NC_000021, complement, nucleotides 38675671-38955488); ETV1 (7p21.3; e.g., GENBANK™ Accession No. NC_000007, complement, nucleotides 13897379-13995289), EWS (22q12.2; e.g., GENBANK™ Accession No. NC_000022, nucleotides 27994271-28026505); FLI1 (11q24.1-q24.3; e.g., GENBANK™ Accession No. NC_000011, nucleotides 128069199-128187521), PAX3 (2q35-q37; e.g., GENBANK™ Accession No. NC_000002, complement, nucleotides 222772851-222871944), PAX7 (1p36.2-p36.12; e.g., GENBANK™ Accession No. NC_000001, nucleotides 18830087-18935219), PTEN (10q23.3; e.g., GENBANK™ Accession No. NC_000010, nucleotides 89613175-89716382), AKT2 (19q13.1-q13.2; e.g., GENBANK™ Accession No. NC_000019, complement, nucleotides 45431556-45483036), MYCL1 (1p34.2; e.g., GENBANK™ Accession No. NC_000001, complement, nucleotides 40133685-40140274), REL (2p13-p12; e.g., GENBANK™ Accession No. NC_000002, nucleotides 60962256-61003682) and CSF1R (5q33-q35; e.g., GENBANK™ Accession No. NC_000005, complement, nucleotides 149413051-149473128).

In other examples, a target protein is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. For example, the target peptide, polypeptide or protein can be selected from the genome of an oncogenic or pathogenic virus, a bacterium or an intracellular parasite (such as *Plasmodium falciparum* and other *Plasmodium* species, *Leishmania* (sp.), *Cryptosporidium parvum*, *Entamoeba histolytica*, and *Giardia lamblia*, as well as *Toxoplasma, Eimeria, Theileria,* and *Babesia* species).

In some examples, the target protein is produced from a nucleic acid sequence (e.g., genomic target nucleic acid sequence) from a viral genome. Exemplary viruses and corresponding genomic sequences (GENBANK™ RefSeq Accession No. in parentheses) include human adenovirus A (NC_001460), human adenovirus B (NC_004001), human adenovirus C(NC_001405), human adenovirus D (NC_002067), human adenovirus E (NC_003266), human adenovirus F (NC_001454), human astrovirus (NC_001943), human BK polyomavirus (V01109; GI:60851) human bocavirus (NC_007455), human coronavirus 229E (NC_002645), human coronavirus HKU1 (NC_006577), human coronavirus NL63 (NC_005831), human coronavirus OC43 (NC_005147), human enterovirus A (NC_001612), human enterovirus B (NC_001472), human enterovirus C(NC_001428), human enterovirus D (NC_001430), human erythrovirus V9 (NC_004295), human foamy virus (NC_001736), human herpesvirus 1 (Herpes simplex virus type 1) (NC_001806), human herpesvirus 2 (Herpes simplex virus type 2) (NC_001798), human herpesvirus 3 (Varicella zoster virus) (NC_001348), human herpesvirus 4 type 1 (Epstein-Barr virus type 1) (NC_007605), human herpesvirus 4 type 2 (Epstein-Barr virus type 2) (NC_009334), human herpesvirus 5 strain AD169 (NC_001347), human herpesvirus 5 strain Merlin Strain (NC_006273), human herpesvirus 6A (NC_001664), human herpesvirus 6B (NC_000898), human herpesvirus 7 (NC_001716), human herpesvirus 8 type M (NC_003409), human herpesvirus 8 type P(NC_009333), human immunodeficiency virus 1 (NC_001802), human immunodeficiency virus 2 (NC_001722), human metapneumovirus (NC_004148), human papillomavirus-1 (NC_001356), human papillomavirus-18 (NC_001357), human papillomavirus-2 (NC_001352), human papillomavirus-54 (NC_001676), human papillomavirus-61 (NC_001694), human papillomavirus-c and 90 (NC_004104), human papillomavirus RTRX7 (NC_004761), human papillomavirus type 10 (NC_001576), human papillomavirus type 101 (NC_008189), human papillomavirus type 103 (NC_008188), human papillomavirus type 107 (NC_009239), human papillomavirus type 16 (NC_001526), human papillomavirus type 24 (NC_001683), human papillomavirus type 26 (NC_001583), human papillomavirus type 32 (NC_001586), human papillomavirus type 34 (NC_001587), human papillomavirus type 4 (NC_001457), human papillomavirus type 41 (NC_001354), human papillomavirus type 48 (NC_001690), human papillomavirus type 49 (NC_001591), human papillomavirus type 5 (NC_001531), human papillomavirus type 50 (NC_001691), human papillomavirus type 53 (NC_001593), human papillomavirus type 60 (NC_001693), human papillomavirus type 63 (NC_001458), human papillomavirus type 6b (NC_001355), human papillomavirus type 7 (NC_001595), human papillomavirus type 71 (NC_002644), human papillomavirus type 9 (NC_001596), human papillomavirus type 92 (NC_004500), human papillomavirus type 96 (NC_005134), human parainfluenza virus 1 (NC_003461), human parainfluenza virus 2 (NC_003443), human parainfluenza virus 3 (NC_001796), human parechovirus (NC_001897), human parvovirus 4 (NC_007018), human parvovirus B19 (NC_000883), human respiratory syncytial virus (NC_001781), human rhinovirus A (NC_001617), human rhinovirus B (NC_001490), human spumaretrovirus (NC_001795), human T-lymphotropic virus 1 (NC_001436), human T-lymphotropic virus 2 (NC_001488).

In certain examples, the target protein is produced from a nucleic acid sequence (e.g., genomic target nucleic acid sequence) from an oncogenic virus, such as Epstein-Barr Virus (EBV) or a Human Papilloma Virus (HPV, e.g., HPV16, HPV18). In other examples, the target protein produced from a nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV).

D. Sample Preparation

The tissue samples described herein can be prepared using any method now known or hereafter developed in the art. Generally, tissue samples are prepared by fixing and embedding the tissue in a medium.

In some examples, an embedding medium is used. An embedding medium is an inert material in which tissues and/or cells are embedded to help preserve them for future analysis. Embedding also enables tissue samples to be sliced into thin sections. Embedding media include, but are not limited to, paraffin, celloidin, OCT™ compound, agar, plastics, or acrylics.

Many embedding media are hydrophobic; therefore, the inert material may need to be removed prior to histological or cytological analysis, which utilizes primarily hydrophilic reagents. The term deparaffinization or dewaxing is broadly used herein to refer to the partial or complete removal of any type of embedding medium from a biological sample. For example, paraffin-embedded tissue sections are dewaxed by passage through organic solvents, such as toluene, xylene, limonene, or other suitable solvents.

The process of fixing a sample can vary. Fixing a tissue sample preserves cells and tissue constituents in as close to a life-like state as possible and allows them to undergo preparative procedures without significant change. Fixation arrests the autolysis and bacterial decomposition processes that begin upon cell death, and stabilizes the cellular and tissue constituents so that they withstand the subsequent stages of tissue processing, such as for IHC or ISH.

Tissues can be fixed by any suitable process, including perfusion or by submersion in a fixative. Fixatives can be classified as cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation). Additives may also be included in the fixative, such as buffers, detergents, tannic acid, phenol, metal salts (such as zinc chloride, zinc sulfate, and lithium salts), and lanthanum.

The most commonly used fixative in preparing samples for IHC is formaldehyde, generally in the form of a formalin solution (4% formaldehyde in a buffer solution, referred to as 10% buffered formalin). In one example, the fixative is 10% neutral buffered formalin.

E. Counterstaining

Counterstaining is a method of post-treating the samples after they have already been stained with agents to detect one or more targets, such that their structures can be more readily visualized under a microscope. For example, a counterstain is optionally used prior to coverslipping to render the immunohistochemical stain more distinct. Counterstains differ in color from a primary stain. Numerous counterstains are well known, such as hematoxylin, eosin, methyl green, methylene blue, Giemsa, Alcian blue, and Nuclear Fast Red.

In some examples, more than one stain can be mixed together to produce the counterstain. This provides flexibility and the ability to choose stains. For example, a first stain, can be selected for the mixture that has a particular attribute, but yet does not have a different desired attribute. A second stain can be added to the mixture that displays the missing desired attribute. For example, toluidine blue, DAPI, and pontamine sky blue can be mixed together to form a counterstain.

F. Imaging

Certain aspects, or all, of the disclosed embodiments can be automated, and facilitated by computer analysis and/or image analysis system. In some applications, precise color ratios are measured. In some embodiments, light microscopy is utilized for image analysis. Certain disclosed embodiments involve acquiring digital images. This can be done by coupling a digital camera to a microscope. Digital images obtained of stained samples are analyzed using image analysis software. Color can be measured in several different ways. For example, color can be measured as red, blue, and green values; hue, saturation, and intensity values; and/or by measuring a specific wavelength or range of wavelengths using a spectral imaging camera.

One disclosed embodiment involves using brightfield imaging with chromogenic dyes. White light in the visible spectrum is transmitted through the dye. The dye absorbs light of certain wavelengths and transmits other wavelengths. This changes the light from white to colored depending on the specific wavelengths of light transmitted.

The samples also can be evaluated qualitatively and semi-quantitatively. Qualitative assessment includes assessing the staining intensity, identifying the positively-staining cells and the intracellular compartments involved in staining, and evaluating the overall sample or slide quality. Separate evaluations are performed on the test samples and this analysis can include a comparison to known average values to determine if the samples represent an abnormal state.

G. Kits

Disclosed embodiments provide, in part, kits for carrying out various embodiments of the method of the invention. Examples of such kits include those useful for cholesterol analyses, pregnancy kits, cancer diagnostic kits, etc. In some embodiments, the kit includes a pyrimidine analog and/or a pyridine analog having a formula as described in Section A.

In some embodiments, the kit includes an enzyme, such as an oxido reductase or a peroxidase, such as horseradish peroxidase or glutathione peroxidase. In some examples, the kit includes a specific binding moiety, such as an antibody or a nucleic acid that specifically binds to a target molecule. In some examples, the specific binding moiety and the enzyme are bound together.

In some embodiments, the kit includes a detectable moiety capable of being detected using deposition or fluorescent techniques, or an enzyme substrate that produces the detectable moiety after reaction with the enzyme. In some examples, the detectable moiety is a fluorophore (such as a fluorescein, a luminophores, a coumarin, a BODIPY dye, a resorufin, or a rhodamine), a hapten (sach as oxazole, pyrazole, thiazole, benzofurazan, triterpene, urea, thiourea, nitroaryl, rotenoid, coumarin, cyclolignan, heterobiaryl, azoaryl, benzodiazepine), a protein, or chromogen (such as 1,3-diaminobenzidine, 3-amino-9-ethylcarbazole, or tetramethylbenzidine). The kit can optionally include at least one optional enhancer, such as a heteroaryl compound, a Group I or Group II metal-containing salt, a boron-containing compound, and a phenol compound, for example those described in Section A.

In some embodiments, the kit includes an oxidant, such as a peroxide, for example hydrogen peroxide.

In some embodiments, the kit includes a surfactant, such as Brij® 35, TWEEN®, Tergitol™, and Triton™.

In some embodiments, the kit includes an antioxidant selected from sodium stannate, sodium metabisulfate, and sodium bisulfate.

In some embodiments, the kit includes copper mordant. The kit can include additional components, including antibodies, hapten-labeled probes and other reagents necessary for performing IHC and/or ISH by chromogenic detection.

Such kits may be used, for example, by a clinician or physician as an aid to selecting an appropriate therapy for a particular patient or for diagnostic purposes.

Particular embodiments concern using kits comprising an inhibitor, such as 3% $H_2O_2$; a Universal Multimer HRP, such as goat anti-mouse/rabbit conjugated to HRP; a peroxide, such as 0.03% $H_2O_2$; a chromogen, such as DAB; and a copper mordant. This kit is referred to as ultraView™, and it can be used in combination with the disclosed enhancers.

H. Automated Embodiments

A person of ordinary skill in the art will appreciate that embodiments of the method disclosed herein for chromogenic detection of two or more molecules can be automated. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. published application Nos. 20030211630 and 20040052685, each of which is incorporated herein by reference. Particular embodiments of the procedures were conducted using various automated processes.

IV. Working Examples

The following examples are provided to illustrate certain specific features of working embodiments. The scope of the present invention is not limited to those features exemplified by the following examples.

Example 1

IHC Tissue Staining with Imidazole

Figure 2:
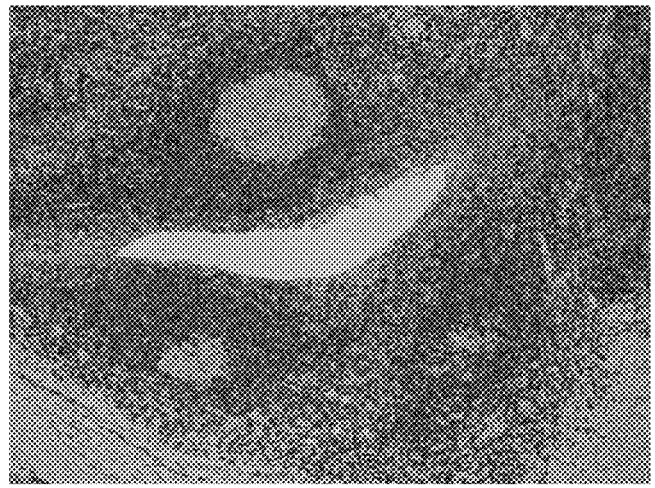
FIG. 2 is a digital image showing the use of 10 mM imidazole as a base buffer in the diaminobenzidine (DAB) staining solution for IHC staining of bcl2 on tonsil tissue.

The IHC staining of bcl2 on tonsil was performed using the ultraView™ Universal DAB Chromogen enhanced with imidazole. Imidazole (10 mM-100 mM) significantly increased the DAB staining intensity (See FIGS. 1 and 2). However, as the desired DAB signal increased so did the observed background signal. Higher concentrations of imidazole proved to be incompatible causing DAB to precipitate from the reformulated DAB Chromogen solution.

Example 2

Kinetic Screening of Enhancers

A plate assay was developed to independently screen potential compounds and better understand the observed enhanced DAB deposition as demonstrated in Example 1. The additives were directly added to a well containing the necessary reagents from the ultraView™ Detection Kit (VMSI 760-500: 253-4290, 253-4292 and 253-4293) in 1× Reaction Buffer (VMSI 950-300) and 0.1% fish gelatin. Fish gelatin was used to help disperse the oxidized DAB and inhibit its precipitation from solution. The ultraView™ Detection Kit was diluted to measure the formation of oxidized DAB by UV-VIS at 455 nm. Additives were tested at set concentrations to determine enhancement in the DAB oxidation reaction. The data were graphed, and the apparent maximum velocity ($V_{max}$) was calculated at each additive concentration level.

Figure 3:
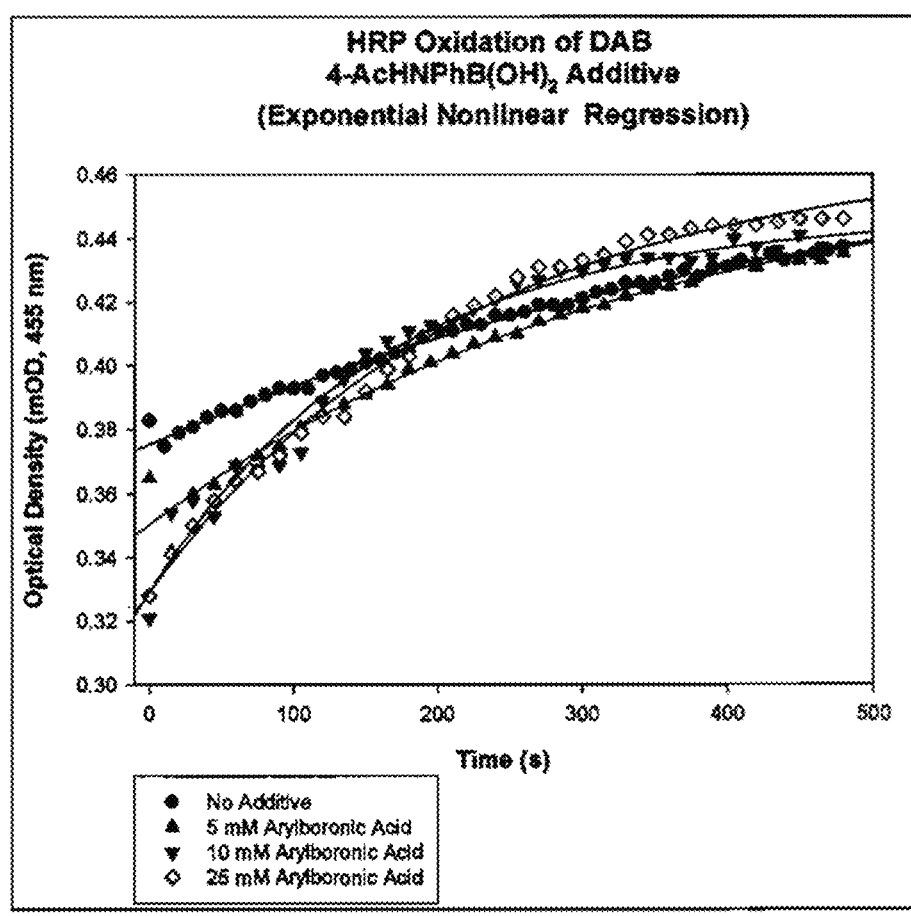
FIG. 3 is a graph showing the influence of 4-acetylamidophenyl boronic acid on the apparent $V_{max}$ for HRP-oxidized DAB when added to the ultraView™ Detection Kit. The optical density of oxidized DAB was monitored at 455 nm.
Figure 4:
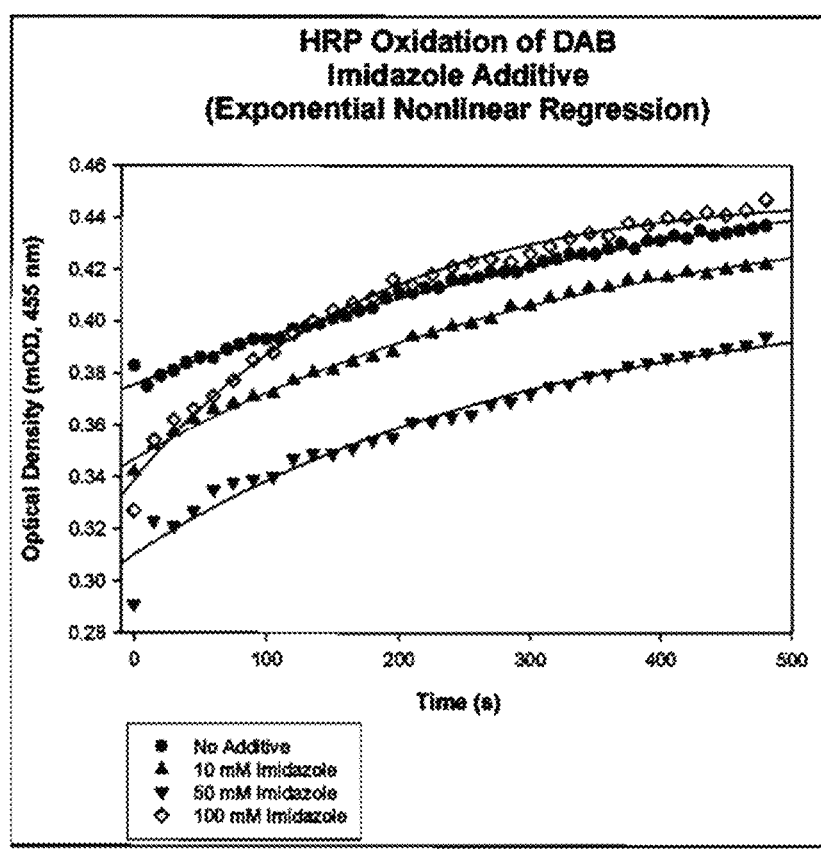
FIG. 4 is a graph showing the influence of imidazole on the apparent $V_{max}$ for horseradish peroxidase- (HRP-) oxidized DAB when added to the ultraView™ Detection Kit. The optical density of oxidized DAB was monitored at 455 nm.

Initial testing of 4-acetylamidophenyl boronic acid and imidazole demonstrated an increased reaction velocity for HRP as the concentration of either additive was increased (See FIGS. 3 and 4, respectively). The apparent $V_{max}$ for HRP-oxidized DAB was 18.5 mOD/minute with no enhancement. The addition of 10 mM imidazole increased the apparent $V_{max}$ by 56%, and 10 mM of 4-acetylamidophenyl boronic acid increased the apparent $V_{max}$ by 77%. (Percent increase $V_{max}$=[(Enhanced $V_{max}$−uView $V_{max}$)/uView $V_{max}$]×100%).

Figure 6:
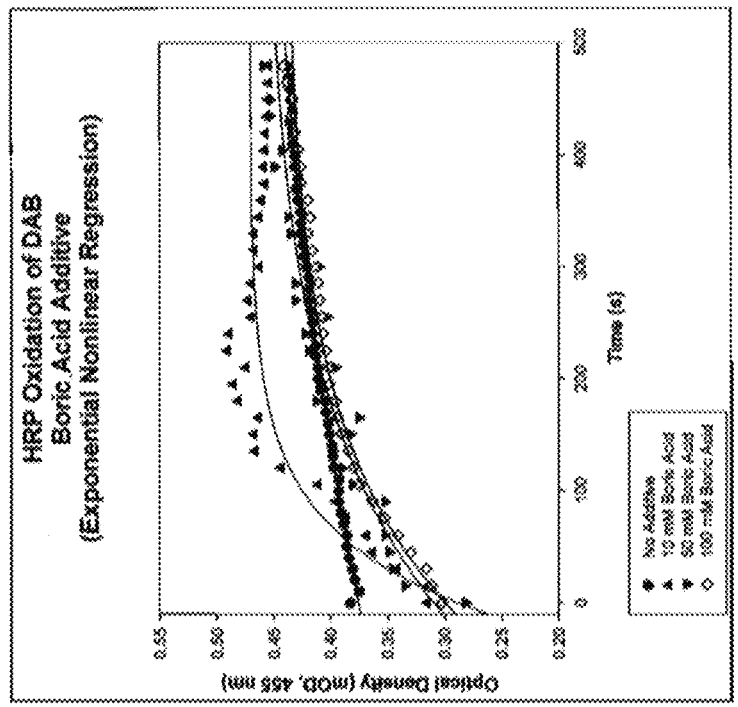
FIG. 6 is a graph showing the influence of boric acid on the apparent $V_{max}$ for HRP-oxidized DAB when added to the ultraView™ Detection Kit. The optical density of oxidized DAB was monitored at 455 nm.
Figure 5:
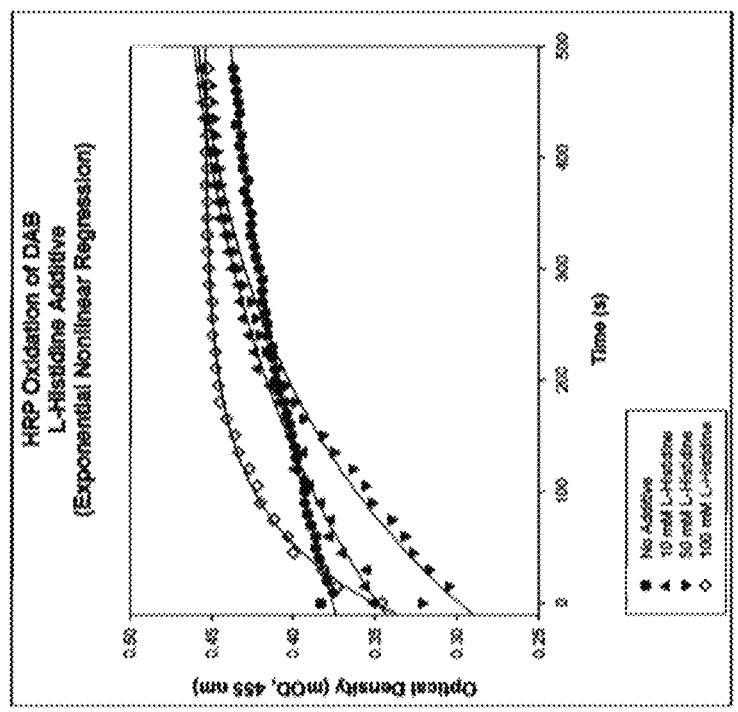
FIG. 5 is a graph showing the influence of L-histidine on the apparent $V_{max}$ for HRP-oxidized DAB when added to the ultraView™ Detection Kit. The optical density of oxidized DAB was monitored at 455 nm.

Spurred by the above results, other buffers that could be used as potential enhancers were examined. In addition to conceptual use of imidazole analogs, L-histidine facilitated peroxide mediated oxidation reactions were explored. 50 mM of L-histidine increased the apparent $V_{max}$ of HRP by 138% (see FIG. 5). As with higher concentration of imidazole, 50 mM L-histidine also caused the precipitation of DAB from the reformulated DAB Chromogen solution. A concentration of 10 mM L-histidine was utilized with DAB reformulations. The apparent $V_{max}$ of HRP was increased 18% with 10 mM L-histidine. Borate buffers were also tested. The buffering capacity of boric acid is not in the desired pH range (variable pH range from about 1 to about 7.9, final pH ranging from about 2 to about 3) for the DAB formulation because boric acid has an effective pH buffer range of about 8.5 to about 10.2. The addition of 10 mM of boric acid enhanced the apparent $V_{max}$ of HRP by 265%, however at 50 mM, boric acid greatly enhanced the apparent $V_{max}$ of HRP by 592% (see FIG. 6).

Other heterocyclic compounds were examined to find a new class of enhancers that would further increase the apparent velocity of HRP. Pyrimidine analogs were discovered to be a novel class of enhancers. A summary of the assay results for all enhancers of HRP-mediated DAB oxidation can be found in Table 1.

TABLE 1

Influence of enhancers on the apparent $V_{max}$ for HRP-oxidized DAB when added to the ultraView ™ Detection Kit.

| Enhancer | Concentration (mM) | Vmax (mOD/min) | Coeff Reg | Enhancer | Concentration (mM) | Vmax (mOD/min) | Coeff Reg |
|---|---|---|---|---|---|---|---|
| No Enhancer | n/a | 18.50 | 0.985 | No Enhancer | n/a | 18.50 | 0.985 |
| Boric Acid | 10 | 67.47 | 0.989 | Thymine | 10 | 82.00 | 0.984 |
|  | 50 | 128.00 | 0.935 |  | 50 (sol) | 86.00 | 0.896 |
|  | 100 | 47.60 (sat) | 0.999 |  | 100 (sol) | 74.00 | 0.990 |
| Calcium Chloride | 5 | 43.50 | 0.984 | Cytosine | 10 | 36.00 | 0.931 |
|  | 10 | 52.50 | 0.999 |  | 50 (sol) | 66.00 | 0.857 |
|  | 20 | 57.00 | 0.998 |  | 100 (sol) | n/a (1) | n/a (1) |
| 4-AcHNPhB(OH)2 | 5 | 21.20 | 0.971 | Uracil | 10 | 52.00 | 0.942 |
|  | 10 | 32.80 | 0.975 |  | 50 (sol) | 72.00 | 0.933 |
|  | 20 | 32.00 | 0.977 |  | 100 (sol) | n/a (1) | n/a (1) |
| Imidazole | 10 | 28.80 | 0.982 | 2-Thiobarbituric | 10 | 54.00 | 0.964 |
|  | 50 | 38.80 | 0.967 | Acid | 50 | 56.00 | 0.911 |
|  | 100 | 70.00 | 0.954 |  | 100 | 76.00 | 0.920 |

TABLE 1-continued

Influence of enhancers on the apparent $V_{max}$ for HRP-oxidized DAB when added to the ultraView™ Detection Kit.

| Enhancer | Concentration (mM) | Vmax (mOD/min) | Coeff Reg | Enhancer | Concentration (mM) | Vmax (mOD/min) | Coeff Reg |
|---|---|---|---|---|---|---|---|
| Thiazole | 10 | 66.40 | 0.993 | Pyrimidine-N-oxide | 10 | 104.00 | 2 pt |
|  | 50 | 27.00 (sat) | 0.989 |  | 50 | 104.00 | 2 pt |
|  | 100 | 27.05 (sat) | 0.972 |  | 100 | 36.00 (sat) | 2 pt |
| Oxazole | 10 | 24.00 | 0.995 | TEMPO | 0.13% (8 mM) | 18.00 | 0.993 |
|  | 50 | 40.00 | 0.961 |  | 0.25% (16 mM) | 24.80 | 0.914 |
|  | 100 | 18.00 (sat) | 0.998 |  | 0.50% (32 mM) | 21.20 | 0.959 |
| Pyrimidine | 10 | 104.00 | 0.961 | NMO | 0.13% (10.7 mM) | 33.60 | 0.933 |
|  | 50 | 124.00 | 0.968 |  | 0.25% (21.3 mM) | 43.60 | 0.988 |
|  | 100 | 36.80 (sat) | 0.983 |  | 0.50% (42.7 mM) | 51.60 | 0.971 |
| L-Histidine | 10 | 21.84 | 0.973 | L-Tryptophan | 10 | 30.00 | 0.994 |
|  | 50 | 44.00 | 0.999 |  | 50 | 52.00 | 0.825 |
|  | 100 | 72.00 | 0.961 |  | 100 | 64.00 | 2 pt |
| 2-Hydroxypyrimidine | 10 | 144.00 | 2 pt | 2-Hydroxypyridine | 10 | 47.67 | 2 pt |
|  | 50 | 156.00 | 2 pt |  | 50 | 18.19 (sat) | 0.970 |
|  | 100 | 148.00 | 2 pt |  | 100 | 15.98 (sat) | 0.985 |

The optical density of oxidized DAB was monitored at 455 nm.
(Sat) = Reaction rate was saturated by the start of UV-VIS analysis.
(Sol) = Solubility issue occurred at room temperature. Heat was required to dissolve the additive in reaction buffer.
(1) Additive was not soluble at room temperature.

Figure 7:
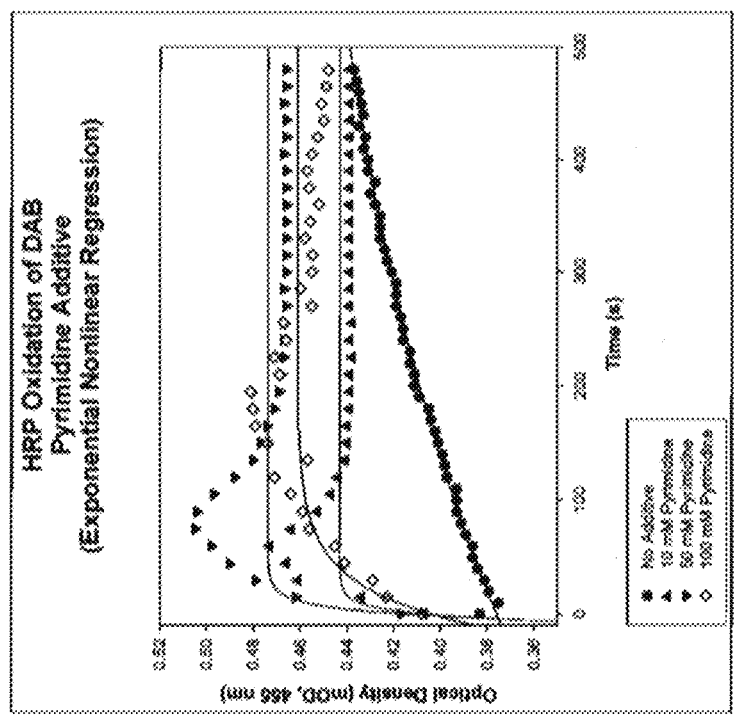
FIG. 7 is a graph showing the influence of pyrimidine on the apparent $V_{max}$ for HRP-oxidized DAB when added to the ultraView™ Detection Kit. The optical density of oxidized DAB was monitored at 455 nm.

The addition of 10 mM of pyrimidine greatly increased the apparent $V_{max}$ of HRP by 462%. This apparent rate increase of DAB oxidation was higher than was observed with other heterocyclic enhancers (imidazole, thiazole and oxazole core structures). Increasing the pyrimidine concentration to 50 mM provided a modest increase in the $V_{max}$ of HRP relative to 10 mM (570%) (see FIG. 7). A reformulation of the DAB chromogen with pyrimidine poses a potential problem due to high vapor pressure (bp≈124° C.). Thus, other pyrimidine analogs were investigated to find a suitable alternative that did not have volatility issues.

Figure 8:
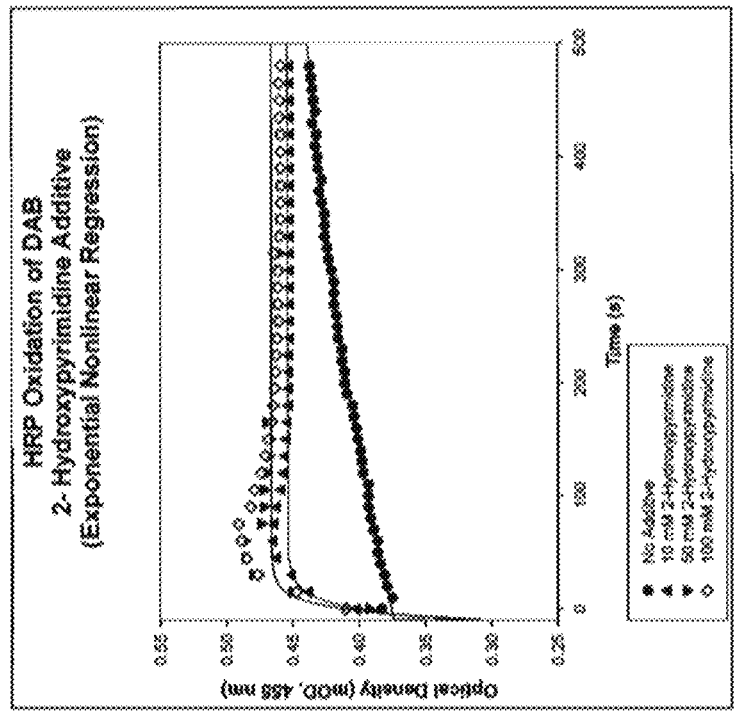
FIG. 8 is a graph showing the influence of 2-hydroxypyrimidine on the apparent $V_{max}$ for HRP-oxidized DAB when added to the ultraView™ Detection Kit. The optical density of oxidized DAB was monitored at 455 nm.

Pyrimidine nucleotide bases (thymine, uracil and cytosine) increased the apparent velocity of HRP, however, they suffer solubility problems in aqueous buffers. Both 2-hydroxypyrimidine (see FIG. 8) and pyrimidine-N-oxide were found to provide similar or increased apparent rates relative to pyrimidine and do not have solubility or volatility problems. Five- and six-member heterocyclic N-oxides have been previously shown to increase the apparent velocity of the HRP-based oxidation of both oligo- and polysaccharides, namely the oxidation of cellulose. Reformulations of DAB with pyrimidine-N-oxide lost functionality and stopped staining with time. However, pyrimidine-N-oxide is still of use in an enhancement solution if added to HRP-mediated oxidation reactions on tissue. In addition to pyrimidine, 10 mM 2-hydroxypyridine increased the apparent $V_{max}$ of HRP (157%). Benzimidazole, methylene blue, phenothiazine, and 4-dimethylaminopyridine provided no enhancement.

Example 3

Synergistic and Antagonistic Effects for Enhancers

Figure 9:
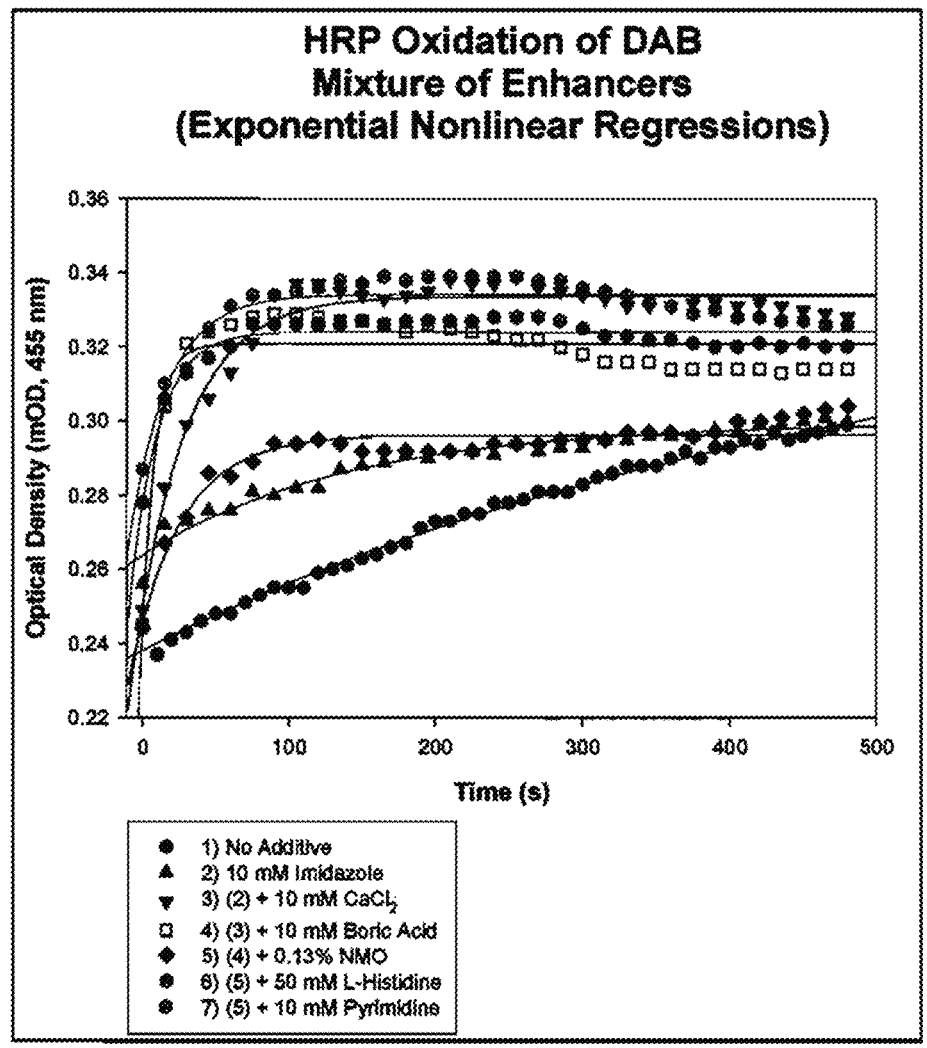
FIG. 9 is a graph showing the influence of potential enhancers on the apparent $V_{max}$ for HRP-oxidized DAB when added sequentially to the ultraView™ Detection Kit. The optical density of oxidized DAB was monitored at 455 nm.

The plate assay from Example 2 was used to examine the potential synergistic and antagonistic effects of each additive on the apparent velocity of HRP-mediated DAB oxidation. The same concentration of reagents from the ultraView™ Detection Kit (VMSI 760-500: 253-4290, 253-4292 and 253-4293) were used in 1× Reaction Buffer™ containing 0.1% fish gelatin for each trial. In each trial, the enhancers were added together one at a time. The results are summarized in FIG. 9 and Table 2.

TABLE 2

Influence of enhancers was evaluated on the apparent $V_{max}$ for HRP-oxidized DAB when added sequentially to the ultraView™ Detection Kit.

| Entry | Enhancer | Vmax (mOD/min) | Coeff Reg |
|---|---|---|---|
| 1 | No Enhancement | 18.50 | 0.985 |
| 2 | 10 mM Imidazole | 34.00 | 0.904 |
| 3 | (2) + 10 mM Calcium Chloride | 96.00 | 0.982 |
| 4 | (3) + 10 mM Boric Acid | 138.00 | 0.915 |
| 5 | (4) + 10.7 mM NMO | 84.00 | 2 pt |
| 6 | (5) + 50 mM L-Histidine | 92.00 | 2 pt |
| 7 | (5) + 10 mM Pyrimidine | 140.00 | 2 pt |

The optical density of oxidized DAB was monitored at 455 nm. (NMO = 4-methylmorpholine N-oxide).

As previously shown in Table 1, 10 mM boric acid increased the apparent velocity of HRP by 265%. The addition of calcium chloride to HRP assays was shown to increase the stability and apparent velocity of HRP. The addition of both 10 mM calcium chloride and 10 mM boric acid to the assay containing 10 mM imidazole synergistically increased the apparent velocity of HRP.

Morpholine-N-oxide increased the apparent velocity of HRP reactions (see Table 1); however, when added to assay mixture 4 (see Table 2, Entry 5), an antagonistic effect was observed. The addition of either 50 mM of L-histidine or 10 mM pyrimidine to reaction mixture 5 (Table 2, Entries 6 and 7) increased the apparent velocity of HRP. These data support screening the use of N-oxides in an enhancement solution. Pyrimidine-N-oxide can be used in combination with L-histidine to increase the deposition of DAB in IHC tissue staining (see FIG. 11).

Example 4

IHC Tissue Staining with Enhancers

IHC staining was performed for bcl2 on tonsil tissue using enhanced DAB chromogen solutions to further examine enhancer synergistic effects on DAB deposition. A pathology scoring summary for IHC staining is shown in Table 3. Reader 1 performed all pathology evaluations during the same period of time. Reader 2 performed the evaluations in batches when the slides were initially produced and accounts for some variability in scoring.

TABLE 3

Pathology scoring summary for IHC staining of bcl2 on tonsil tissue using ultraView ™ DAB staining and enhanced DAB chromogen solutions.

| Solution tested | Reader 1 | BG1 | Reader 2 | BG2 |
|---|---|---|---|---|
| ultraView DAB | 3.75 | 0.25 | 3 | 0.25 |
| Base 1 | 3.75 | 0.5 | 4++ | 0.5 |
| Base 1 w/10 mM pyrimidine | 4 | 0.5 | 4++ | 0 |
| Base 1 w/10 mM CaCl2 | 4 | 0.5 | 3.5 | 0.5 |
| Base 1 w/5 mM phosphite | 3.75 | 0.25 | 4 | 0.5 |
| Base 2 | 4 | 0.5 | 4 | 0.75 |
| Base 2 w/10 mM pyrimidine | 4+ | 0.5 | 3.5 | 0.5 |
| Base 2 w/10 mM CaCl2 | 4 | 0.5 | 3.5 | 0.5 |
| Base 2 w/5 mM phosphite | 4+ | 0.5 | 3.75 | 0.5 |
| Base 3 | 4+ | 0.75 | 3.5 | 0.5 |
| Base 3 w/10 mM CaCl2 | 4+ | 0.5 | 3.5 | 0.5 |
| Base 3 w/5 mM phosphite | 4+ | 0.75 | 3.75 | 0.5 |
| Base 4 | 4 | 0.5 | 4 | 0.25 |
| Base 4 w/10 mM Boric acid | 4 | 0.5 | 3.5 | 0 |
| Base 2 w/10 mM Boric Acid | 4 | 0.5 | 4 | 0.25 |
| Base 4 w/10 mM thymine | 4 | 0.5 | 4 | 0.25 |
| Base 4 w/10 mM 2-OH pyrimidine | 3.75 | 0.5 | 4 | 0.5 |
| Base 4 w/10 mM L-Tryptophan | 4 | 0.5 | 4 | 0.25 |
| Base 4 w/10 mM Pyrimidine N-oxide | 4+ | 0.5 | 4 | 0.25 |
| Base 4 w/10 mM CaCl2 | 4 | 0.75 | 3.5 | 0.25 |
| Base 4a | 4+ | 0.75 | 3.5 | 0.5 |
| Base 4a w/10 mM pyrimidine | 4+ | 0.75 | 3.5 | 0.25 |
| Base 4a w/10 mM 2-OH Pyridine | 4+ | 0.75 | 4++ | 0 |

All compositions of the new base buffers contain 5.5 mM of 3,3-diaminobenzidine tetrahydrochloride (DAB•4 HCl) and 0.05% wt. Brij ® 35 (peroxidase free). [Base 1: 50 mM L-histidine (pH = 6.5); Base 2: 10 mM imidazole (pH = 6.5); Base 3: 2.43 mM citric acid, 5.13 mM sodium phosphate (pH = 5.3); Base 4: 10 mM L-histidine (pH = 6.5); Base 4a: 10 mM L-histidine (pH = 6.5), 10 mM calcium chloride, 10 mM boric acid.]

Two general observations were noted. First, a maximum apparent rate enhancement for the HRP deposition of DAB was achieved through the combination of 2-3 enhancer components. Additional enhancers did not increase the signal intensity of the strongest DAB staining on tissue; however, the percentage of cells stained with the highest signal intensity increased throughout the tissue. This observation was largely due to the limited number of turnovers observed by HRP-DAB oxidation reactions on tissue. Secondly, enhancers which increased the HRP-mediated DAB oxidation in the plate assay provided more discrete deposition of DAB on tissue. The DAB staining was generally less diffuse.

Figure 10:
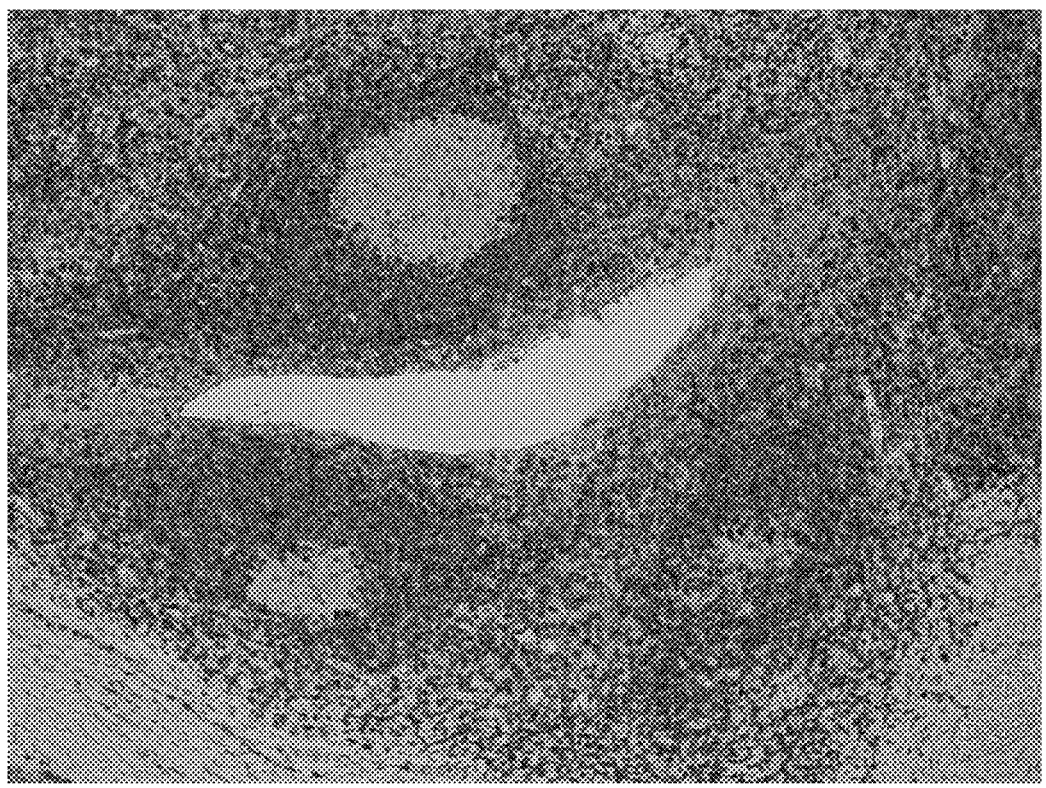
FIG. 10 is a digital image of ultraView™ DAB staining of bcl2 (tonsil) tissue using a 10 mM imidazole based DAB chromogen solution.
Figure 11:
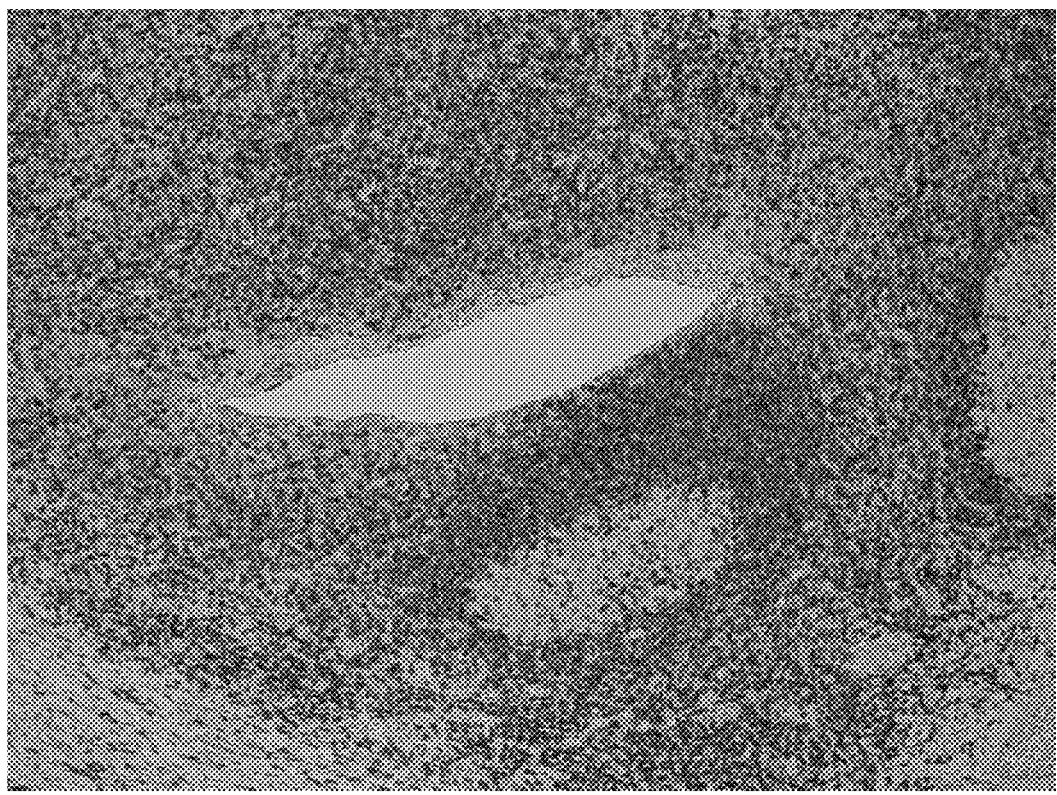
FIG. 11 is a digital image of ultraView™ DAB staining of bcl2 tissue using a 10 mM L-histidine based DAB chromogen solution.

The IHC staining of bcl2 (tonsil) using a 5.5 mM DAB solution formulated with either 10 mM imidazole or 10 mM L-histidine and 0.05% Brij® 35 is shown in FIGS. 10 and 11. Pathological review of the DAB staining with the 10 mM L-histidine showed a similar intensity to that afforded with 10 mM imidazole.

Figure 12:
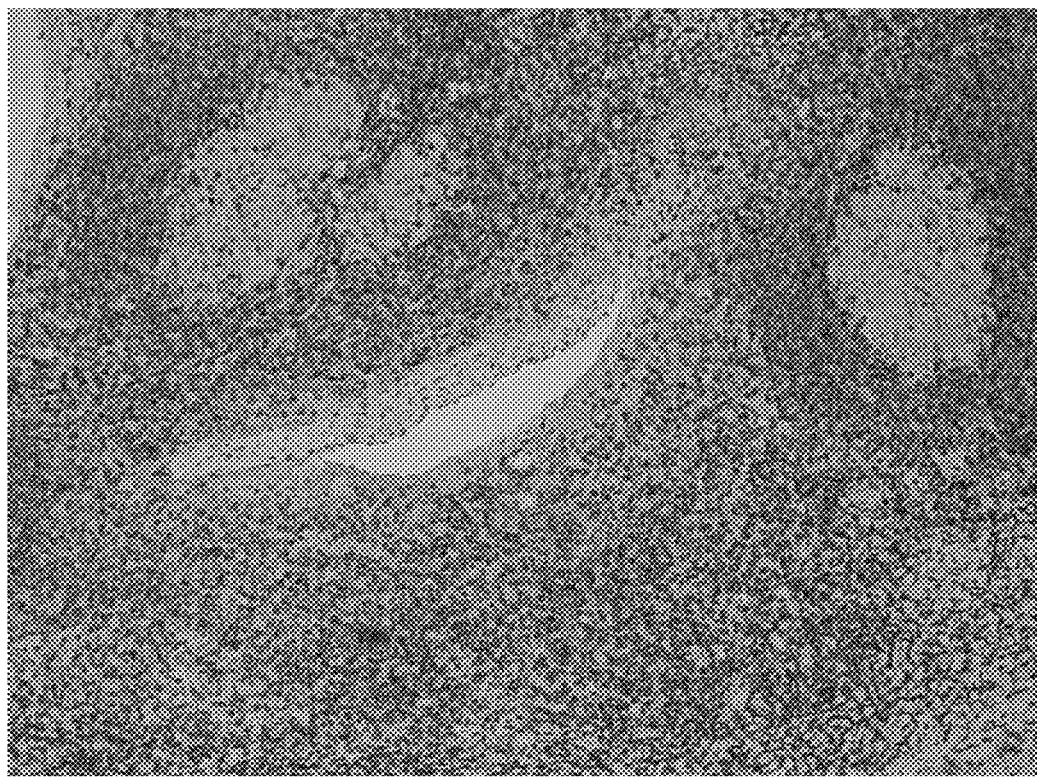
FIG. 12 is a digital image of ultraView™ DAB staining of bcl2 tissue using a 10 mM pyrimidine-N-oxide in 10 mM L-histidine based DAB chromogen solution.
Figure 13:
FIG. 13 is a digital image of ultraView™ DAB staining of bcl2 tissue using a 10 mM 2-hydroxypyrimidine in 10 mM L-histidine based DAB chromogen solution.
Figure 14:
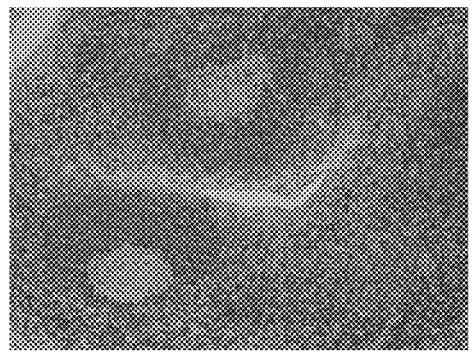
FIGS. 14-17 are digital images of IHC staining of bcl2 on tonsil tissue using a standard VMSI ultraView™ Detection Kit with or without DAB "enhancement solutions." DAB enhancement solutions.
Figure 15:
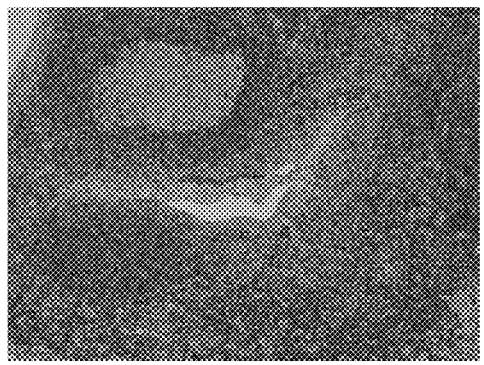

Tissue staining with 5.5 mM DAB solutions formulated with either 10 mM pyrimidine-N-oxide or 10 mM 2-hydroxypyrimidine in 10 mM L-histidine and 0.05% Brij® 35 is shown in FIGS. 12 and 13. Pathological review of DAB staining with both enhancer solutions showed that pyrimidine-N-oxide provided the best DAB signal to background noise ratio for the two enhancers.

Figure 16:
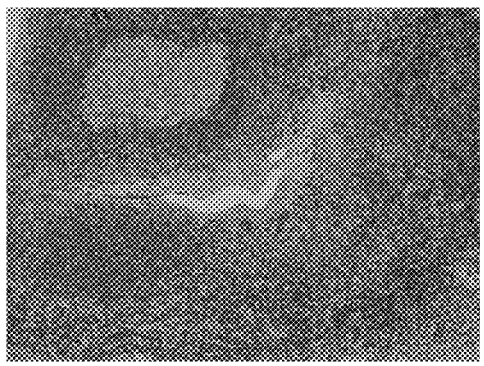
Figure 17:
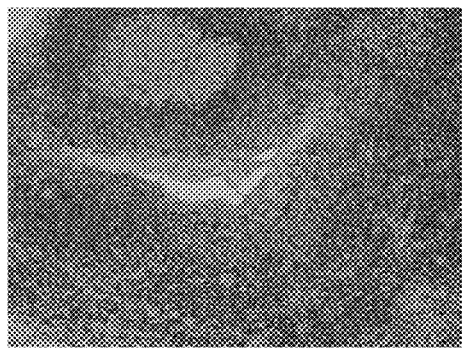

The IHC staining of bcl2 on tonsil tissue was evaluated using the addition of an "enhancement solution" to a standard ultraView™ detection kit. No correction was made to the concentration of the ultraView™ reagents to compensate for dilution of the enhancement solution (see FIGS. 14-17). 50 mM L-histidine and 10 mM pyrimidine (FIG. 16) was picked by pathology reader 1 as a preferred DAB stain as shown in Table 3. 100 mM imidazole and 50 mM boric acid increased DAB deposition, but reduced the dynamic range of the DAB signal and increased the serum background. A lower concentration of enhancers would increase the DAB signal dynamic range. A solution of 10 mM L-histidine, 10 mM 2-hydroxypyridine, 10 mM calcium chloride, 10 mM boric acid showed a lower DAB signal when reformulating a DAB solution (last row of Table 3). 10 mM pyrimidine-N-oxide is a prime candidate for an enhancement solution.

Example 5

Michaelis-Menton Kinetics

Figure 19:
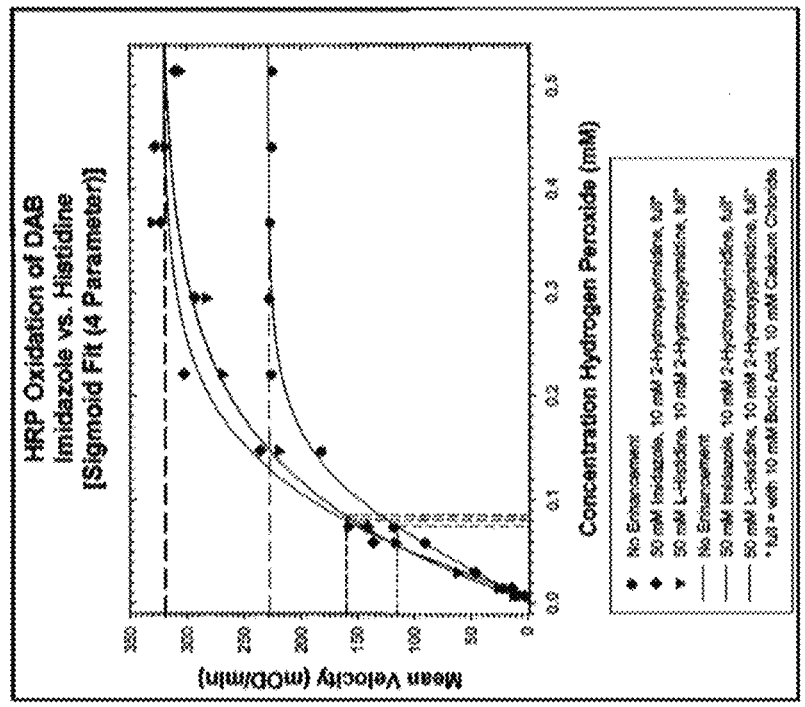
FIG. 19 is a graph showing the influence of imidazole and L-histidine DAB chromogen solutions on the apparent $V_{max}$ for HRP-oxidized DAB when combined with 10 mM 2-hydroxypyrimidine, 10 mM boric acid and 10 mM calcium chloride. The optical density of oxidized DAB was monitored at 455 nm.
Figure 18:
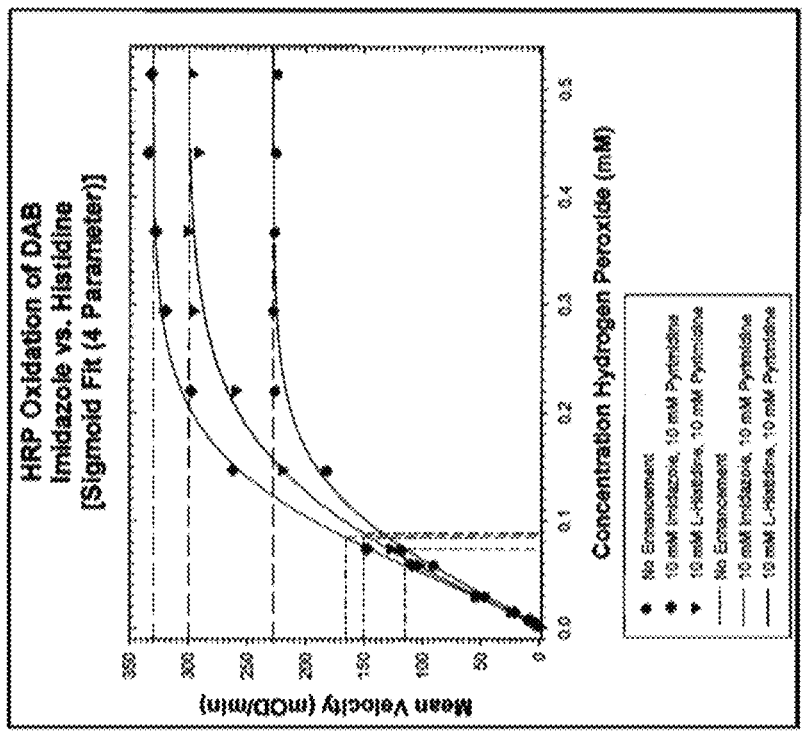
FIG. 18 is a graph showing the influence of imidazole and L-histidine DAB chromogen solutions on the apparent $V_{max}$ for HRP-oxidized DAB when combined with 10 mM pyrimidine. The optical density of oxidized DAB was monitored at 455 nm.

To further study the synergistic effect in the increased apparent $V_{max}$ for HRP-oxidized DAB, Michaelis-Menten kinetics were calculated for the best enhanced DAB chromogen mixtures in Table 3. A 1:32 dilution of the ultraView™ HRP multimer was reacted with a variable concentration of hydrogen peroxide (0.015 µM-0.514 µM) to saturate the apparent velocity of HRP. Initially, both imidazole and L-histidine were examined with 10 mM pyrimidine (see FIG. 18) and 10 mM 2-hydroxypyrimidine (see FIG. 19). Similar $K_m$ values calculated at $½V_{max}$, but imidazole afforded a higher apparent $V_{max}$ than L-histidine (see Table 4). The definition of $V_{max}=k_{cat} \cdot [E]_{total}$ when the enzyme substrate concentration was at saturation levels. When the concentration of enzyme was kept constant, the apparent $V_{max}$ is proportional to $k_{cat}$ (the apparent turnover for HRP or the first order rate constant). Imidazole increased the apparent turnover of HRP higher then L-histidine.

TABLE 4

Influence of enhancers on the apparent $V_{max}$ for HRP-oxidized DAB when combined with 50 mM imidazole, 10 mM calcium chloride and 10 mM boric acid.

| Enhancer | Vmax (mOD/min) | Km |
|---|---|---|
| No Enhancer | 228 | 0.073 |
| Buffer with 10 mM Pyrimidine | | |
| 10 mM Imidazole | 330 | 0.085 |
| 10 mM L-Histidine | 300 | 0.088 |
| Buffer with 10 mM 2-Hydroxypyrimidine | | |
| 50 mM Imidazole | 320 | 0.081 |
| 50 mM L-Histidine | 317 | 0.084 |
| Enhancer in 50 mM Imidazole, 10 mM Calcium Chloride, 10 mM Boric Acid | | |
| 50 mM Pyrimidine | 326 | 0.082 |
| 10 mM 2-Hydroxypyrimidine | 320 | 0.081 |
| 10 mM 2-Hydroxypyridine | 383 | 1.001 |
| Pyrimidine-N-Oxide | 374 | 0.098 |

$K_m$ was determined at $½V_{max}$.

Figure 20:
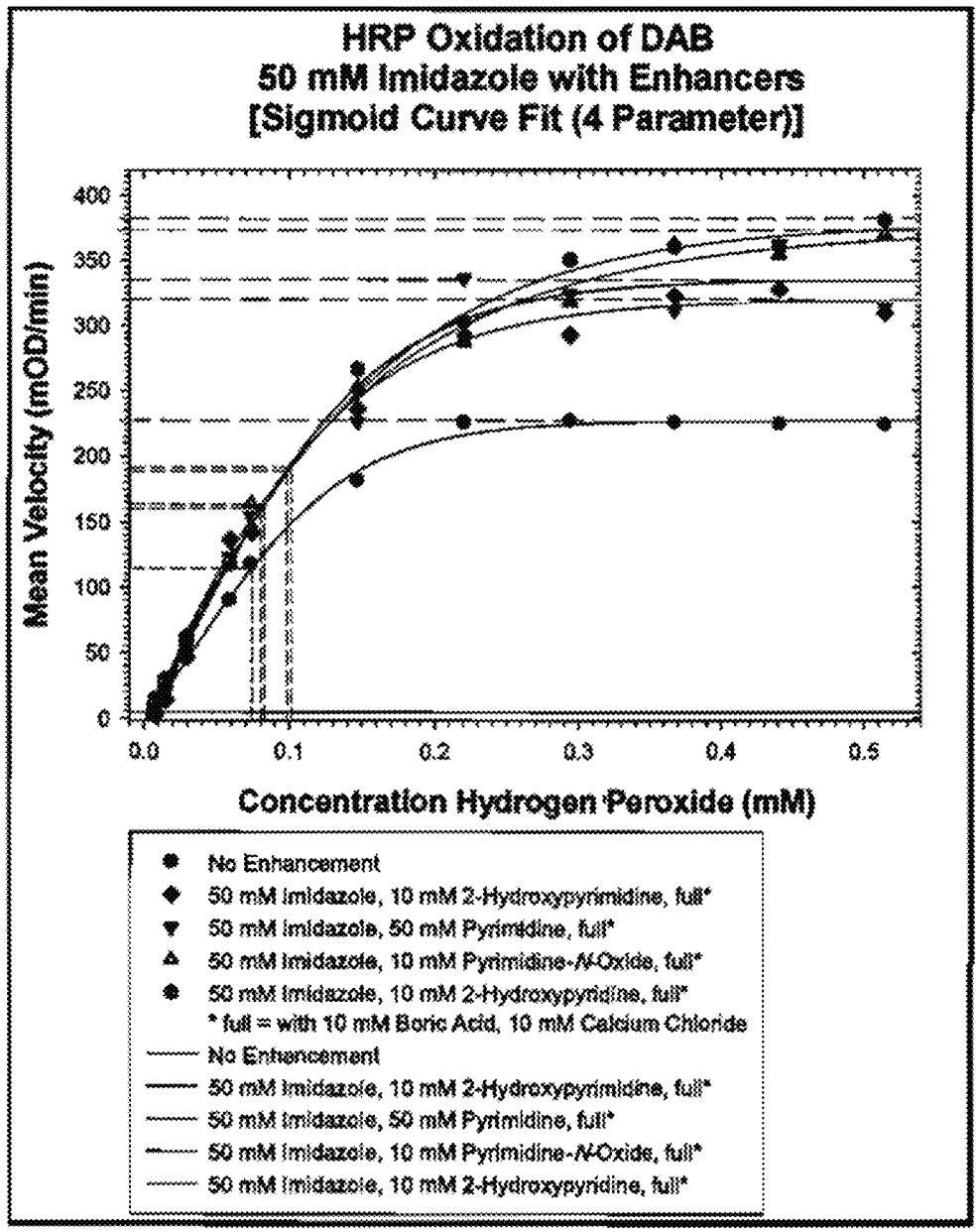
FIG. 20 is a graph showing the influence of enhancers on the apparent $V_{max}$ for HRP-oxidized DAB when combined with 50 mM imidazole, 10 mM calcium chloride and 10 mM boric acid. The optical density of oxidized DAB was monitored at 455 nm.

Imidazole DAB chromogen solutions with enhancers were screened for influence on the apparent $V_{max}$ of HRP (see FIG. 20 and Table 4). 50 mM imidazole was used for a larger enhancement of DAB oxidation. The enhancement effect on the apparent turnover of HRP was 10 mM 2-hydroxypyridine>10 mM pyrimidine-N-oxide>50 mM pyrimidine>10 mM 2-hydroxypyrimidine. These results paralleled with the observed staining intensities discussed in Table 3.

Using the DAB Chromogen solutions in Table 4, a plate assay was performed using variable concentrations of the ultraView™ HRP Multimer (0.27 pg-68.8 pg). The apparent $V_{max}$ was monitored and the data reported as a percent increase or decrease in the apparent $V_{max}$ as compared to unenhanced reactions (see Table 5). An increase in the apparent $V_{max}$ of HRP was observed as the concentration of HRP was lowered. The magnitude of change increased at lower HRP concentrations. These data confirmed the results from Table 4 where imidazole provided a larger apparent $V_{max}$ relative to L-histidine. This effect was observed for a majority of concentrations.

TABLE 5

Influence of buffer salts and enhancers on the apparent $V_{max}$ for HRP-oxidized DAB when added to the ultraView Detection Kit ™.

| Base Salt | Enhancer | \multicolumn{9}{c}{Concentration of HRP (pg)} | | | | | | | | |
|---|---|---|---|---|---|---|---|---|---|---|
| | | 68.8 | 34.4 | 17.2 | 8.59 | 4.3 | 2.15 | 1.07 | 0.54 | 0.27 |
| 10 mM Histidine | A | −12 | −9 | −7 | 3 | −3 | −7 | −6 | 27 | 9 |
| 10 mM Imidazole | A | −22 | −15 | 2 | 19 | 22 | 11 | 12 | 43 | 145 |
| 50 mM Histidine | B | −3 | −10 | 0 | 13 | 10 | 0 | 4 | 35 | 9 |
| 50 mM Imidazole | B | −3 | 14 | 16 | 30 | 28 | 18 | 34 | 71 | 32 |
| 50 mM Imidazole | C | −3 | 3 | 12 | 19 | 18 | 17 | 20 | 89 | 97 |
| 50 mM Imidazole | D | −2 | 11 | 10 | 20 | 31 | 30 | 62 | 58 | 46 |

The optical density of oxidized DAB was monitored at 455 nm. [Enhancers: (A) = 10 mM pyrimidine; (B) = 10 mM 2-hydroxypyrimidine, 10 mM calcium chloride, 10 mM boric acid; (C) = 10 mM 2-hydroxypyridine, 10 mM calcium chloride, 10 mM boric acid; (D) = 10 mM pyrimidine-N-oxide, 10 mM calcium chloride, 10 mM boric acid].

Example 6

ISH Tissue Staining with Enhancers

Figure 21:
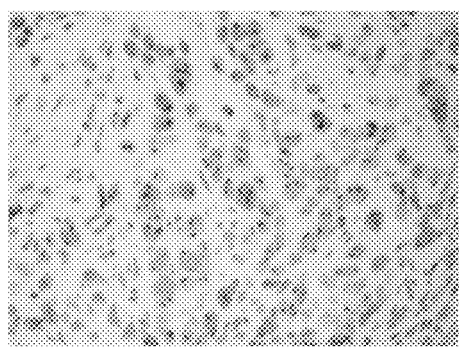
FIG. 21 is a digital image of DAB ISH staining of HER-2 probe on HER-2 3-in-1 mouse xenographs of HER-2 positive CaLu3 carcinoma cell lines with the ultraView™ Detection System.
Figure 22:
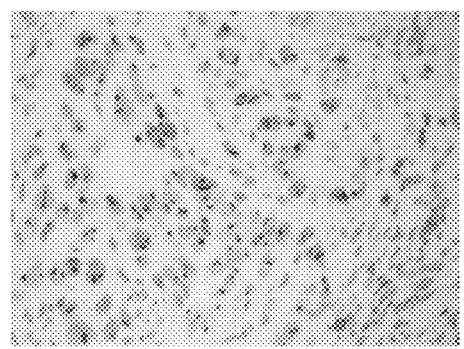
FIG. 22 is a digital image of DAB ISH staining of HER-2 probe on HER-2 3-in-1 mouse xenographs of HER-2 positive CaLu3 carcinoma cell lines with a DAB chromogen solution and 10 mM L-histidine enhancement.

ISH tissue staining was examined using enhanced DAB solutions. HER-2 3-in-1 mouse xenografts of HER-2 positive carcinoma cell lines CaLu3, ZR-75-1 and MCF7 were treated with HER2 DNA probe (VMSI 480-4495) and stained with the ultraView™ DAB Chromogen solution or an enhanced DAB Chromogen solution containing 10 mM L-histidine (see FIGS. 21-22). 10 mM L-histidine increased the deposition of DAB in the ISH staining of CaLu3 carcinoma cells having an over expression of HER2. The increased DAB deposition was marginal for the strongest ISH signals, but signal intensity for the weaker DAB signals was raised throughout the tissue. The same observation was made with enhanced DAB deposition in IHC.

Example 7

TSA Tissue Staining with Enhancers

Enhanced DAB deposition was evaluated on a TSA-IHC tissue staining of bcl2 in tonsil tissue. The bcl2 antigen was stained with TSA using TA-HQ deposition for 4 minutes after a 16 minute incubation of the bcl2 primary Ab. Tyramide deposition was performed with and without 10 mM 2-hydroxypyrimidine. DAB deposition was performed with the ultraView™ DAB Chromogen solution or a DAB Chromogen solution containing 10 mM L-histidine (see FIGS. 23-26). 10 mM L-histidine increased the DAB deposition on tissue.

Figure 27:
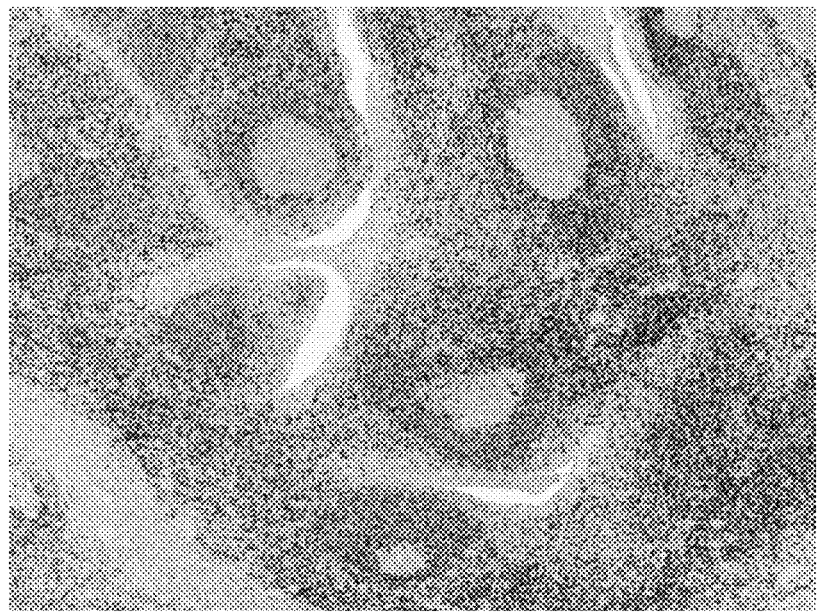
FIGS. 27-28 are digital images of IHC staining of bcl2 on tonsil tissue using the tyramide amplification system for tyramide deposition with 10 mM 2-hydroxypyrimidine (FIG. 27) and without enhancement of HRP oxidation (FIG. 28).
Figure 28:
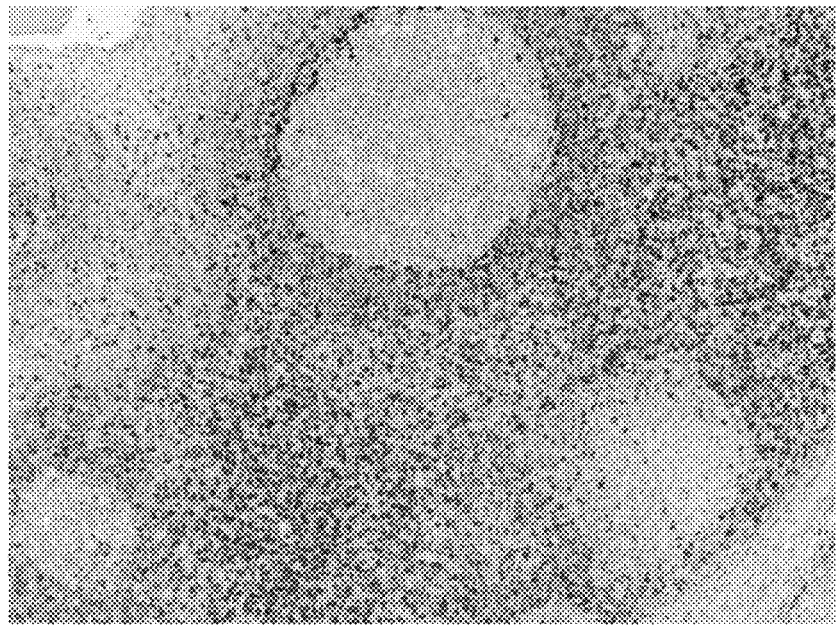

In a parallel study, the bcl2 antigen was stained with TSA using TA-HQ deposition for 4 minutes after an 8 minute incubation of the bcl2 primary Ab (see FIGS. 27 and 28). 10 mM 2-hydroxypyrimidine increased the tyramide deposition and thus increased the DAB deposition. The percent of cells stained with DAB increased in areas with low bcl2 antigen expression.

Example 8

18s Riboprobe Staining

Formalin fixed paraffin embedded CaLu-3 xenograft tissues were mounted on Superfrost® slides, deparaffinized and antigen retrieved using RiboClear™ denaturant (a component of RiboMap® kit; Ventana® p/n 760-102) for 12 minute incubation, CC2 reagent (Ventana® p/n 950-123), and protease 3 for 8 minute incubation (Ventana® p/n 760-2020). Following retrieval, two drops (200 μL) of a NP haptenylated anti-sense or sense strand 18s probe was dispensed onto a slide, denatured at 80° C. for 8 minutes, and hybridized at 65° C. for 6 hours. Following hybridization, slides were washed 3 times using 0.1×SSC at 75° C. for 8 minutes; each NP haptenylated probe was detected using 5 μg of a Mouse anti-NP HRP conjugate followed by 100 μL of each a 55 μL tyramide-HQ conjugate and $H_2O_2$ (component of ultraView™ DAB kit Ventana® p/n 760-500) and incubated for 12 minutes. The deposited tyramide-HQ was detected using 0.5 μg of a mouse anti HQ HRP conjugate followed by a drop of DAB (5.5 mM DAB; 0.05% Brij® 35; 10 mM L-histidine; 10 mM 2-hydroxypyridine) and $H_2O_2$ incubating on the slide for 8 minutes. ultraView™ DAB was used as the reference. After rinsing the slides in reaction buffer, 100 μL of copper (component of ultraView™ DAB kit) was applied to slide for 4 minutes. Slides were counterstained using Hematoxylin II (Ventana® p/n 790-2208) and Bluing Reagent (Ventana® p/n 760-2037). The slides were dehydrated using gradient alcohols, cover slipped and viewed using a bright field microscope. The comparison of the enhancer treated sample and the ultraView™ sample are shown in FIGS. 29 and 30, respectively.

Example 9

HPV Staining

Figure 31:
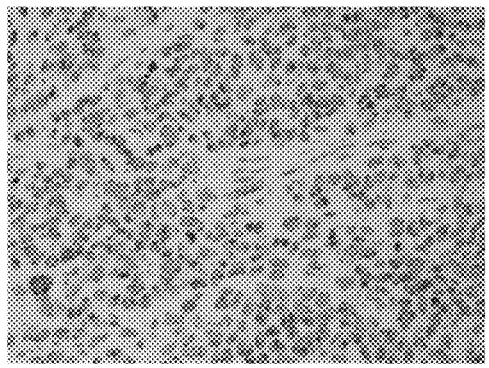
FIG. 31 is a digital image of IHC staining of HPV on CaSki xenograft tissues with haptenylated HPV probe, and an enhanced DAB with both 10 mM 2-hydroxypyridine and 10 mM L-histidine.
Figure 32:
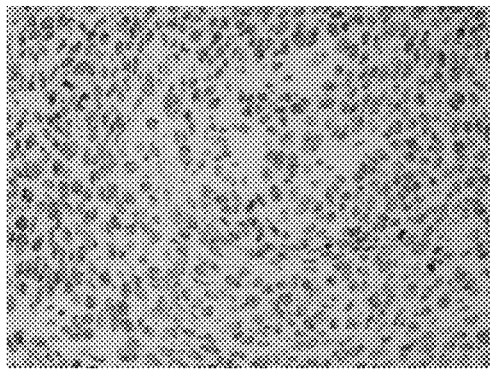
FIG. 32 is a digital image of IHC staining of HPV on CaSki xenograft tissues with haptenylated HPV probe and no enhancement.
Figure 33:
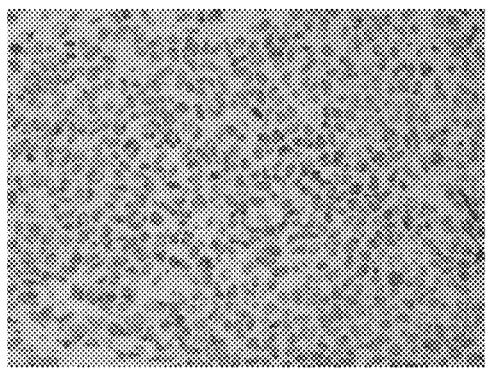
FIG. 33 is a digital image of IHC staining of HPV on HeLa xenograft tissues with haptenylated HPV probe, and an enhanced DAB with both 10 mM 2-hydroxypyridine and 10 mM L-histidine.
Figure 34:
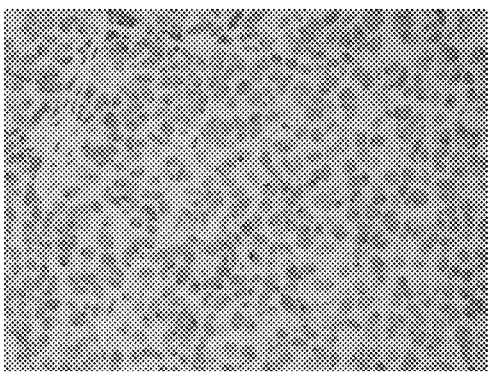
FIG. 34 is a digital image of IHC staining of HPV on HeLa xenograft tissues with haptenylated HPV probe and no enhancement.
Figure 35:
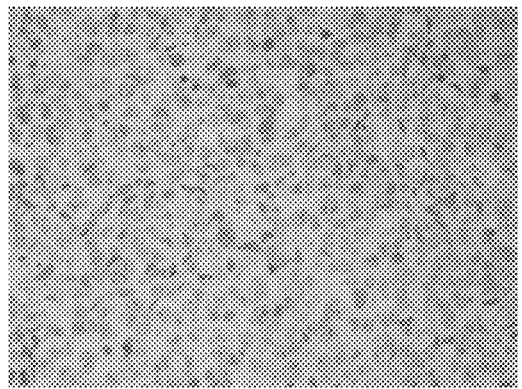
FIG. 35 is a digital image of IHC staining of HPV on C33 xenograft tissues with haptenylated HPV probe, and an enhanced DAB with both 10 mM 2-hydroxypyridine and 10 mM L-histidine.
Figure 36:
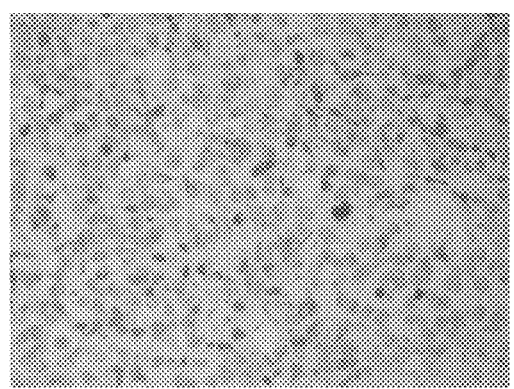
FIG. 36 is a digital image of IHC staining of HPV on C33 xenograft tissues with haptenylated HPV probe and no enhancement.

Formalin fixed paraffin embedded C33, HeLa and CaSki xenograft tissues were mounted on Superfrost slides, deparaffinized and antigen retrieved using CC2 reagent (Ventana® p/n 950-123), and protease 3 for an 8 minute incubation (Ventana® p/n 760-2020). Following retrieval, three drops (300 μL) of SISH Hyb Buffer (a component of ultraView™ SISH detection kit p/n 780-001) and three drops of DIG haptenylated HPV probe was dispensed onto a slide, denatured at 75° C. for 8 minutes, and hybridized at 44° C. for 6 hours. Following hybridization, slides were washed 3 times using 0.1×SSC at 64° C. for 8 minutes. The DIG haptenylated probe was detected using 3 µg of a Mouse anti-DIG HRP conjugate followed by DAB (5.5 mM DAB; 0.05% Brij® 35; 10 mM L-histidine; 10 mM 2-hydroxypyridine) and $H_2O_2$ (component of ultraView™DAB kit Ventana p/n 760-500) incubating on the slide for 8 minutes. ultraView™ DAB was used as the reference. After rinsing the slides in reaction buffer, 100 µL of copper (component of ultraView™ DAB kit) was applied to slide for 4 minutes. Slides were counterstained using Hematoxylin II (Ventana® p/n 790-2208) and Bluing Reagent (Ventana® p/n760-2037). The slides were dehydrated using gradient alcohols, cover slipped and viewed using a bright field microscope. The comparison of the enhancer treated sample and the ultraView™ sample are shown in FIG. 31 versus 32, 33 versus 34, and 35 versus 36, respectively.

Example 10

CD20 DAB Staining

Figure 37:
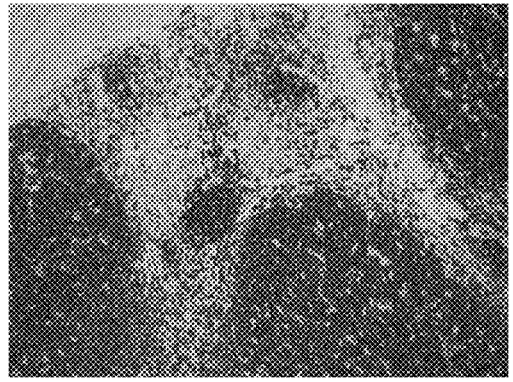
FIG. 37 is a digital image of IHC staining of CD20 on tonsil tissues with anti-CD20 probe, and enhanced DAB with both 10 mM 2-hydroxypyridine and 10 mM L-histidine.
Figure 38:
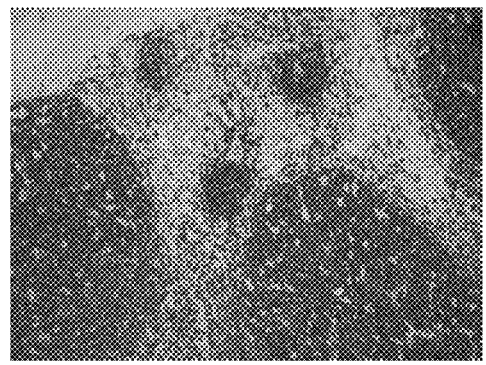
FIG. 38 is a digital image of IHC staining of CD20 on tonsil tissues with anti-CD 20 probe and no enhancement.

Formalin fixed paraffin embedded tonsil tissue was mounted on Superfrost slides, deparaffinized and antigen retrieved using CC1 bulk reagent (Ventana® p/n 950-124). Following retrieval, one drop (100 µL) of UV Inhibitor (a component of the ultraView™ DAB kit) was dispensed onto a slide and incubated for 8 minutes. Following the incubation of the Inhibitor, 1 drop of the mouse anti-CD20 (clone L-26; Ventana® p/n 760-2531) was dispensed onto the slide and incubated for 16 minutes. Following 2 rinses with reaction buffer, the CD20 antibody was detected using 1 drop of the ultraView™ universal HRP conjugate (a component of the ultraView™ DAB kit) and incubated on the slide for 8 minutes. One drop of DAB (5.5 mM DAB; 0.05% Brij® 35; 10 mM L-histidine; 10 mM 2-hydroxypyridine) and $H_2O_2$ were each added to the slides and incubated for 8 minutes. ultraView™ DAB was used as the reference. After rinsing the slides in reaction buffer, 100 µL of copper (component of ultraView™ DAB kit) was applied to slide for 4 minutes. Slides were counterstained using Hematoxylin II (Ventana® p/n 790-2208) and Bluing Reagent (Ventana® p/n760-2037). The slides were dehydrated using gradient alcohols, cover slipped and viewed using a bright field microscope. The comparison of the enhancer treated sample and the ultraView™ sample are shown in FIGS. 37 and 38, respectively.

Example 11

CD20 and Ki-67 AEC Staining

Figure 39:
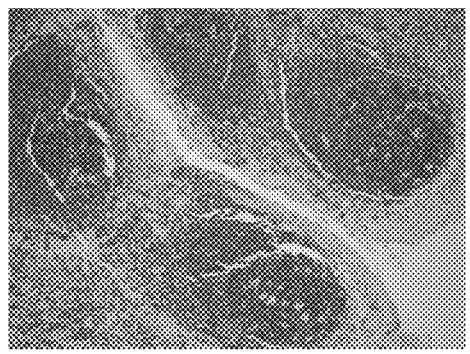
FIG. 39 is a digital image of IHC staining of CD20 on tonsil tissues with anti-CD20 probe, and AEC deposition enhanced with 50 mM L-histidine and 10 mM 2-hydroxypyridine.
Figure 40:
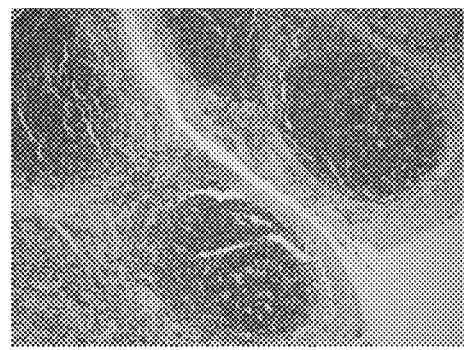
FIG. 40 is a digital image of IHC staining of CD20 on tonsil tissues with anti-CD20 probe and no enhancement.
Figure 41:
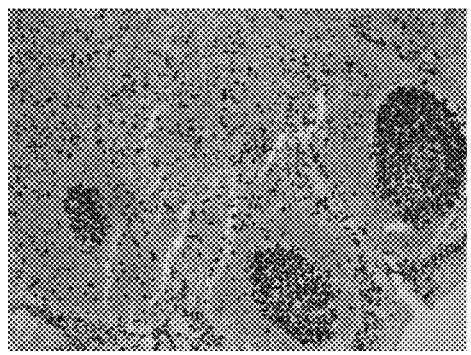
FIG. 41 is a digital image of IHC staining of Ki67 on tonsil tissues with anti-Ki67 probe, and AEC deposition enhanced with 50 mM L-histidine and 10 mM 2-hydroxypyridine.
Figure 42:
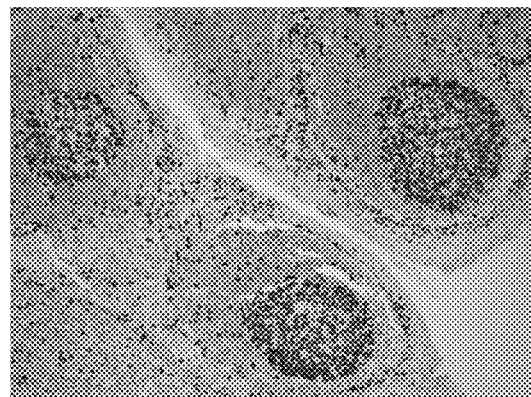
FIG. 42 is a digital image of IHC staining of Ki67 on tonsil tissues with anti-Ki67 probe and no enhancement
Figure 43:
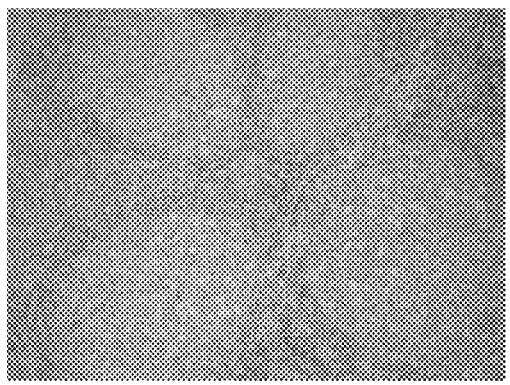
FIGS. 43-46 are digital images of the IHC staining of bcl2 on tonsil tissue using tyramide amplification system with and without enhancement of HRP oxidation for both tyramide and DAB deposition.
Figure 44:
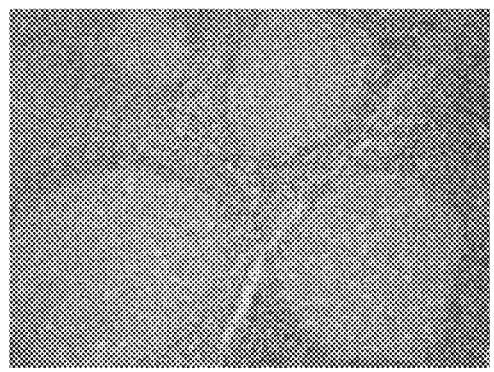
Figure 45:
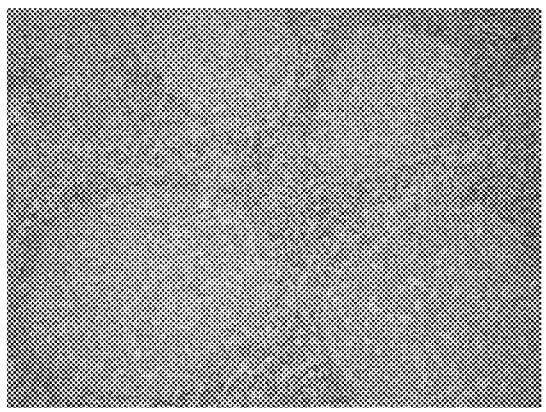
Figure 46:
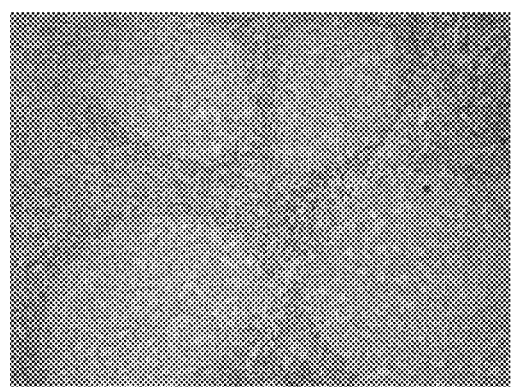

Formalin fixed paraffin embedded tonsil tissue was mounted on Superfrost slides, deparaffinized and antigen retrieved using CC1 bulk reagent (Ventana® p/n 950-124). Following retrieval, one drop (100 µL) of Inhibitor (a component of the AEC kit Ventana® p/n 760-020) was dispensed onto a slide and incubated for 8 minutes. Following the incubation of the Inhibitor, 1 drop of the mouse anti-CD20 (clone L-26; Ventana® p/n 760-2531) or rabbit anti-Ki67 (clone 30-9; Ventana® p/n 790-4286) was dispensed onto the slide and incubated for 16 minutes. Following 2 rinses with reaction buffer, the antibody was detected using 1 drop of the ultraView™ universal HRP conjugate (a component of the ultraView™ DAB kit) and incubated on the slide for 8 minutes. One drop of an Enhancement Solution containing 50 mM L-histidine pH 6.5 and 10 mM 2-hydroxypyridine was added and co-incubated with one drop of each AEC and $H_2O_2$ and incubated for 8 minutes. A slide stained with AEC chromogen without any enhancement was used as the reference. Slides were counterstained using Hematoxylin II (Ventana® p/n 790-2208) and Bluing Reagent (Ventana® p/n760-2037). The slides were allowed to air dry; were cover slipped with an aqueous mounting media and viewed using a bright field microscope. The comparison of the enhancer treated sample and the ultraView™ sample are shown in FIG. 39 versus 40, and 41 versus 42, respectively.

Example 12

Bcl-2 DAB Staining

Formalin fixed paraffin embedded tonsil tissue was mounted on Superfrost slides, deparaffinized and antigen retrieved using CC1 bulk reagent (Ventana® p/n 950-124). Following retrieval, one drop (100 µL) of UV Inhibitor (a component of the ultraView™ DAB kit) was dispensed onto a slide and incubated for 8 minutes. Following the incubation of the Inhibitor, 1 drop of the mouse anti-bcl2 (clone 124; Ventana® p/n 790-4464) was dispensed onto the slide and incubated for 16 minutes. Following 2 rinses with reaction buffer, the bcl2 antibody was detected using 1 drop of the ultraView™ universal HRP conjugate (a component of the ultraView™ DAB kit) and incubated on the slide for 8 minutes. One drop of DAB (5.5 mM DAB; 0.05% Brij® 35; plus any combination of enhancers investigated in table 3) and $H_2O_2$ were each added to the slides and incubated for 8 minutes. ultraView™ DAB was used as the reference. After rinsing the slides in reaction buffer, 100 µL of copper (component of ultraView™ DAB kit) was applied to slide for 4 minutes. Slides were counterstained using Hematoxylin II (Ventana® p/n 790-2208) and Bluing Reagent (Ventana p/n760-2037). The slides were dehydrated using gradient alcohols, cover slipped and viewed using a bright field microscope.

Example 13

Bcl-2-TSA-HQ DAB Staining

Formalin fixed paraffin embedded tonsil tissue was mounted on Superfrost slides, deparaffinized and antigen retrieved using CC1 bulk reagent (Ventana® p/n 950-124). Following retrieval, one drop (100 µL) of UV Inhibitor (a component of the ultraView™ DAB kit) was dispensed onto a slide and incubated for 8 minutes. Following the incubation of the Inhibitor, 1 drop of the mouse anti-bcl2 (clone 124; Ventana® p/n 790-4464) was dispensed onto the slide and incubated for 16 minutes. Following 2 rinses with reaction buffer, the bcl2 antibody was detected using 1 drop of the ultraView™ universal HRP conjugate (a component of the ultraView™ DAB kit) and incubated on the slide for 8 minutes. 100 µL of each a 55 uM tyramide-HQ with and without a 10 mM 2-hydroxypyridine and $H_2O_2$ (component of ultraView™ DAB kit Ventana® p/n 760-500) and incubated for 12 minutes. The deposited tyramide-HQ was detected using 0.5 µg of the mouse anti-HQ HRP conjugate followed by a drop of DAB (5.5 mM DAB; 0.05% Brij® 35; 10 mM L-histidine) and $H_2O_2$ incubating on the slide for 8 minutes. ultraView™ DAB was used as the reference. After rinsing the slides in reaction buffer, 100 µL of copper (component of ultraView™ DAB kit) was applied to slide for 4 minutes. Slides were counterstained using Hematoxylin II (Ventana® p/n 790-2208) and Bluing Reagent (Ventana® p/n760-2037). The slides were dehydrated using gradient alcohols, cover slipped and viewed using a bright field microscope (FIGS. 23-26).

Example 14

Bcl-2-TSA-NP DAB Staining

Formalin fixed paraffin embedded tonsil tissue was mounted on Superfrost slides, deparaffinized and antigen retrieved using CC1 bulk reagent (Ventana p/n 950-124). Following retrieval, one drop (100 μL) of UV Inhibitor (a component of the ultraView™ DAB kit) was dispensed onto a slide and incubated for 8 minutes. Following the incubation of the Inhibitor, 1 drop of the mouse anti-bcl2 (clone 124; Ventana® p/n 790-4464), 1:300 dilution, was dispensed onto the slide and incubated for 16 minutes. Following 2 rinses with reaction buffer, the bcl2 antibody was detected using 1 drop of the ultraView™ universal HRP conjugate (a component of the ultraView™ DAB kit) and incubated on the slide for 8 minutes. 100 μL of each a 5 uM tyramide-NP with and without a 10 mM 2-hydroxypyridine and $H_2O_2$ (component of the ultraView™ DAB kit Ventana® p/n 760-500) and incubated for 12 minutes. The deposited tyramide-HQ was detected using 0.5 μg of the mouse anti-NP HRP conjugate followed by a drop of DAB (5.5 mM DAB; 0.05% Brij® 35; 10 mM L-histidine; 10 mM 2-hydroxypyridine) and $H_2O_2$ incubating on the slide for 8 minutes. ultraView™ DAB was used as the reference. After rinsing the slides in reaction buffer, 100 μl of copper (component of ultraView™ DAB kit) was applied to slide for 4 minutes. Slides were counterstained using Hematoxylin II (Ventana p/n 790-2208) and Bluing Reagent (Ventana p/n760-2037). The slides were dehydrated using gradient alcohols, cover slipped and viewed using a bright field microscope (FIGS. 43-46).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A composition for detecting a target in a sample by proximally depositing a detectable moiety, comprising:
a pyrimidine and/or pyridine deposition enhancer having a formula

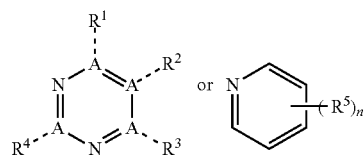

wherein $R^1$, $R^2$, $R^3$, and $R^4$ are independently selected from aliphatic, aryl, halogen, a heteroatom-containing moiety, and hydrogen; $R^1$ and/or $R^3$ can be bound to $R^2$ to form a fused, aromatic ring system; $R^5$ is a heteroatom-containing moiety; A is carbon, a heteroatom other than sulfur, and any combination thereof and n is 1-5;
a second deposition enhancer; and
an enzyme substrate.

2. The composition according to claim 1 where the second deposition enhancer has a formula

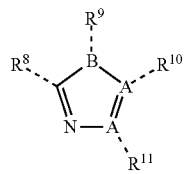

where:
A is carbon, a heteroatom other than sulfur, or any combination thereof;
B is carbon, nitrogen, or oxygen; and
$R^8$, $R^9$, $R^{10}$ and $R^{11}$ independently are aliphatic, aryl, halogen, a heteroatom-containing moiety, hydrogen, or any combination thereof.

3. The composition according to claim 2 where the heteroatom-containing moiety is hydroxyl, ether, silyl ether, ester, carboxylic acid, silyl, phosphonate, phosphine, amide, or $NR^6R^7$ where $R^6$ and $R^7$ independently are hydrogen, aliphatic, aryl, heteroaliphatic, heteroaryl, or any combination thereof.

4. The composition according to claim 2 where A is carbon and B is nitrogen.

5. The composition according to claim 1 where the second deposition enhancer is selected from imidazole, L-histidine, thiazole, oxazole, or any combination thereof.

6. The composition according to claim 1 where the second deposition enhancer has a formula

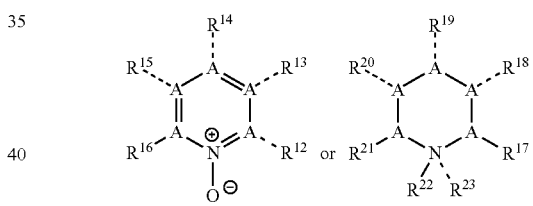

where:
A is carbon, nitrogen, oxygen, or any combination thereof; and
$R^{12}$-$R^{23}$ independently are aliphatic, aryl, halogen, a heteroatom-containing moiety, hydrogen, or any combination thereof.

7. The composition according to claim 6 where the heteroatom-containing moiety is hydroxyl, ether, silyl ether, ester, carboxylic acid, silyl, phosphonate, phosphine, amide, or $NR^6R^7$ where $R^6$ and $R^7$ independently are hydrogen, aliphatic, aryl, heteroaliphatic, heteroaryl, or any combination thereof.

8. The composition according to claim 6 where $R^{22}$ is [O]. or [O]⁻.

9. The composition according to claim 6 where the second deposition enhancer is pyrimidine N-oxide, pyridine N-oxide, N-methyl morpholine (NMO), and 2,2,6,6-tetramethylpiperidine-1-oxyl (TEMPO).

10. The composition according to claim 1 where the second deposition enhancer is an inorganic or organic boronic acid.

11. The composition according to claim 10 where the second deposition enhancer has a formula

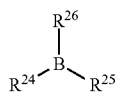

where $R^{24}$, $R^{25}$, and $R^{26}$ independently are aliphatic, aryl, heteroaliphatic, heteroaryl, or any combination thereof.

12. The composition according to claim 11 where two or more of $R^{24}$, $R^{25}$, and $R^{26}$ are hydroxyl, with any remaining $R^{24}$, $R^{25}$, or $R^{26}$ being aliphatic, aryl, heteroaliphatic, or heteroaryl.

13. The composition according to claim 10 where the boronic acid is boric acid, phenyl boronic acid, 4-AcHN-phenyl boronic acid, or any combination thereof.

14. The composition according to claim 1 where the second deposition enhancer is a phenolic compound having a formula

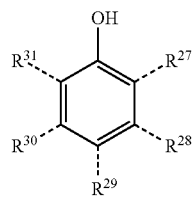

where $R^{27}$, $R^{28}$, $R^{29}$, $R^{30}$, and $R^{31}$ independently are hydrogen, aliphatic, aryl, a heteroatom-containing moiety, halogen, or any combination thereof.

15. The composition according to claim 14 where the heteroatom-containing moiety is hydroxyl, ether, silyl ether, ester, carboxylic acid, silyl, phosphonate, phosphine, amide, or $NR^6R^7$ where $R^6$ and $R^7$ independently are aliphatic, aryl, heteroaliphatic, heteroaryl, hydrogen, or any combination thereof.

16. The composition according to claim 14 where two adjacent groups selected from $R^{27}$, $R^{28}$, $R^{29}$, $R^{30}$, and $R^{31}$ form a fused aromatic or non-aromatic ring system.

17. The composition according to claim 14 where at least one of $R^{27}$, $R^{28}$, $R^{29}$, $R^{30}$, and $R^{31}$ is hydroxyl.

18. The composition according to claim 14 where the phenolic compound is pyrocatechol.

19. The composition according to claim 1 where the second deposition enhancer has a formula

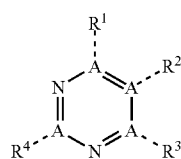

where:
A is carbon, a heteroatom other than sulfur, and combinations thereof; and
$R^1$, $R^2$, $R^3$, and $R^4$ are selected from aliphatic, aryl, halogen, a heteroatom-containing moiety, and hydrogen, or $R^1$ and/or $R^3$ can be bound to $R^2$ to form a fused aromatic ring system.

20. The composition according to claim 1 where the enzyme substrate is selected from 1,3-diaminobenzidine, 3-amino-9-ethylcarbazole, tetramethylbenzidine, a fluorescein, a luminophore, a coumarin, a BODIPY dye, a resorufin, a rhodamine, a tyramide, or a derivative thereof.

21. The composition according to claim 1 wherein the deposition enhancer is selected from 2-hydroxypyridine, pyrimidine or 2-hydroxypyrimidine.

22. A method for detecting a target in a sample by proximally depositing a detectable moiety, comprising:
contacting the sample with a recognition solution, the recognition solution including a specific binding moiety specific to the target;
labeling the specific binding moiety with an enzyme;
contacting the sample with a detection solution, the detection solution comprising an enzymatic substrate so that the detectable moiety deposits proximally to the target in the presence of a first deposition enhancer and a second deposition enhancer, the first deposition enhancer having a formula

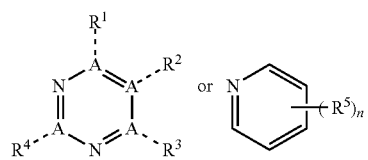

wherein $R^1$, $R^2$, $R^3$, and $R^4$ are independently selected from aliphatic, aryl, halogen, a heteroatom-containing moiety, and hydrogen; $R^1$ and/or $R^3$ can be bound to $R^2$ to form a fused, aromatic ring system; $R^5$ is a heteroatom-containing moiety; A is carbon, a heteroatom other than sulfur, and any combination thereof; and n is 1-5; and
detecting the detectable moiety.

23. The method according to claim 22 where the second deposition enhancer has a formula

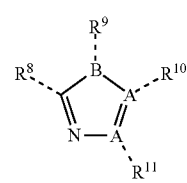

where:
A is carbon, a heteroatom other than sulfur, or any combination thereof;
B is carbon, nitrogen or oxygen; and
$R^8$, $R^9$, $R^{10}$ and $R^{11}$ independently are aliphatic, aryl, halogen, a heteroatom-containing moiety, hydrogen, or any combination thereof.

24. The method according to claim 23 where the heteroatom-containing moiety is hydroxyl, ether, silyl ether, ester, carboxylic acid, silyl, phosphonate, phosphine, amide, or $NR^6R^7$ where $R^6$ and $R^7$ independently are hydrogen, aliphatic, aryl, heteroaliphatic, heteroaryl, or any combination thereof.

25. The method according to claim 23 where A is carbon and B is nitrogen.

26. The method according to claim 22 where the second deposition enhancer is selected from imidazole, L-histidine, thiazole, oxazole, or any combination thereof.

27. The method according to claim 22 where the second deposition enhancer has a formula

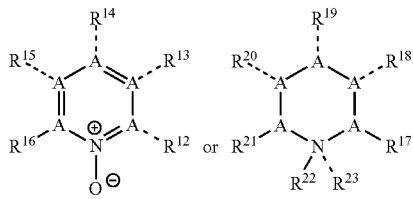

where:
A is carbon, nitrogen, oxygen, or any combination thereof; and
$R^{12}$-$R^{23}$ independently are aliphatic, aryl, halogen, a heteroatom-containing moiety, hydrogen, or any combination thereof.

28. The method according to claim 27 where the heteroatom-containing moiety is hydroxyl, ether, silyl ether, ester, carboxylic acid, silyl, phosphonate, phosphine, amide, or $NR^6R^7$ where $R^6$ and $R^7$ independently are hydrogen, aliphatic, aryl, heteroaliphatic, heteroaryl, or any combination thereof.

29. The method according to claim 27 where $R^{22}$ is [O]. or [O]$^-$.

30. The method according to claim 27 where the second deposition enhancer is pyrimidine N-oxide, pyridine N-oxide, N-methyl morpholine (NMO), and 2,2,6,6-tetramethyl-piperidine-1-oxyl (TEMPO).

31. The method according to claim 22 where the second deposition enhancer is an inorganic or organic boronic acid.

32. The method according to claim 31 where the second deposition enhancer has a formula

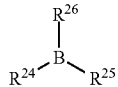

where $R^{24}$, $R^{25}$, and $R^{26}$ independently are aliphatic, aryl, heteroaliphatic, heteroaryl, or any combination thereof.

33. The method according to claim 32 where two or more of $R^{24}$, $R^{25}$, and $R^{26}$ are hydroxyl, with any remaining $R^{24}$, $R^{25}$, or $R^{26}$ being aliphatic, aryl, heteroaliphatic, or heteroaryl.

34. The method according to claim 31 where the second deposition enhancer is boric acid, phenyl boronic acid, 4-AcHN-phenyl boronic acid, or any combination thereof.

35. The method according to claim 22 where the second deposition enhancer is a phenolic compound having a formula

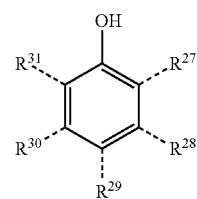

where $R^{27}$, $R^{28}$, $R^{29}$, $R^{30}$, and $R^{31}$ independently are hydrogen, aliphatic, aryl, a heteroatom-containing moiety, halogen, or any combination thereof.

36. The method according to claim 35 where the heteroatom-containing moiety is hydroxyl, ether, silyl ether, ester, carboxylic acid, silyl, phosphonate, phosphine, amide, or $NR^6R^7$ where $R^6$ and $R^7$ independently are hydrogen, aliphatic, aryl, heteroaliphatic, heteroaryl, or any combination thereof.

37. The method according to claim 35 where two adjacent $R^{27}$, $R^{28}$, $R^{29}$, $R^{30}$, and $R^{31}$ groups form a fused aromatic or non-aromatic ring system.

38. The method according to claim 35 where at least one of $R^{27}$, $R^{28}$, $R^{29}$, $R^{30}$, and $R^{31}$ is hydroxyl.

39. The method according to claim 35 where the second deposition enhancer is pyrocatechol.

* * * * *